(12) United States Patent
Heller et al.

(10) Patent No.: US 10,801,928 B2
(45) Date of Patent: Oct. 13, 2020

(54) FLUID SAMPLE COLLECTION SYSTEM FOR PUMPED FLUID SOURCE

(71) Applicant: BESST, INC., San Rafael, CA (US)

(72) Inventors: Noah R. Heller, Fairfax, CA (US); Jacob Aman, San Diego, CA (US); Gaunt Murdock, Crockett, CA (US); Miles Koehler, Oakland, CA (US)

(73) Assignee: BESST, Inc., San Rafael, CA (US)

( * ) Notice: Subject to any disclaimer, the term of this patent is extended or adjusted under 35 U.S.C. 154(b) by 324 days.

(21) Appl. No.: 15/893,369

(22) Filed: Feb. 9, 2018

(65) Prior Publication Data

US 2018/0231439 A1 Aug. 16, 2018

Related U.S. Application Data

(60) Provisional application No. 62/459,996, filed on Feb. 16, 2017.

(51) Int. Cl.
| | |
|---|---|
| *G01N 1/18* | (2006.01) |
| *G01N 33/18* | (2006.01) |
| *G01N 1/28* | (2006.01) |
| *G01N 1/14* | (2006.01) |
| *G01N 1/10* | (2006.01) |

(52) U.S. Cl.
CPC .............. *G01N 1/14* (2013.01); *G01N 1/18* (2013.01); *G01N 1/28* (2013.01); *G01N 33/1826* (2013.01); *G01N 2001/1031* (2013.01)

(58) Field of Classification Search
CPC .. B01D 11/0203; F04B 15/08; F04B 2205/03; F04B 2205/09; F16K 15/183; G01N 1/34; G01N 30/28; G01N 30/02; G01N 30/60; G01N 2001/4061; G01N 2030/6013; G01N 30/82; G01N 1/18; G01N 33/1826; G01N 2001/1031; G01N 1/28; G01N 1/14; G21F 5/015; F05C 2201/0493; G06F 19/3468
See application file for complete search history.

(56) References Cited

U.S. PATENT DOCUMENTS

| | | | | |
|---|---|---|---|---|
| 5,601,707 A | * | 2/1997 | Clay | B01D 11/0203 210/198.2 |
| 2008/0090289 A1 | * | 4/2008 | Denvir | C12M 33/12 435/309.1 |

* cited by examiner

*Primary Examiner* — Brandi N Hopkins
(74) *Attorney, Agent, or Firm* — Roeder & Broder LLP; James P. Broder

(57) ABSTRACT

A fluid sample collection system for directly collecting a fluid sample from a fluid source without exposing the fluid sample to an ambient environment that surrounds the fluid sample collection system includes a fluid collector including (i) a sample vial that is configured to retain fluid from the fluid source, the sample vial including a sample vial body and a vial cap that is selectively coupled and sealed to the sample vial body; (ii) a collector body that defines a passenger vial chamber, the sample vial being positioned at least partially within the passenger vial chamber during collection of the fluid; and (iii) a cap access facilitator that is configured to engage a portion of the sample vial to enable a user to selectively couple the vial cap to the sample vial body to seal the sample vial so that the fluid is retained within the sample vial.

25 Claims, 11 Drawing Sheets

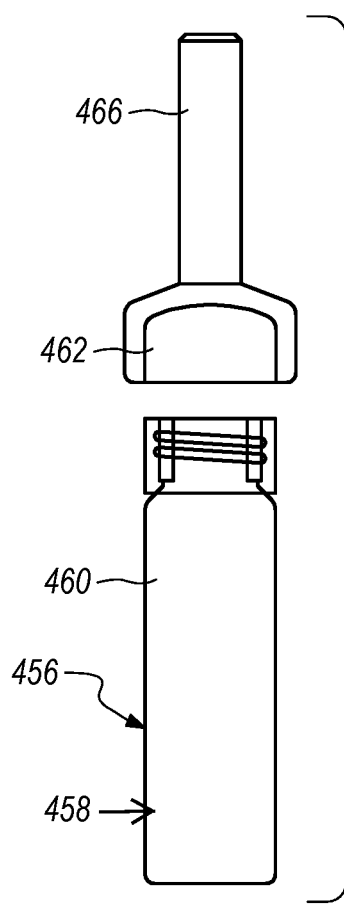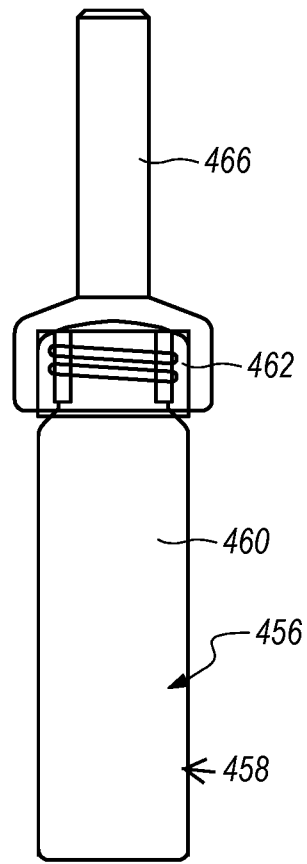
FIG. 5A      FIG. 5B

FLUID SAMPLE COLLECTION SYSTEM FOR PUMPED FLUID SOURCE

RELATED APPLICATION

This application claims priority on U.S. Provisional Application Ser. No. 62/459,996, filed on Feb. 16, 2017, and entitled "FLUID SAMPLE COLLECTION SYSTEM FROM PUMPS IN WELLS". As far as permitted, the contents of U.S. Provisional Application Ser. No. 62/459,996 are incorporated in their entirety herein by reference.

BACKGROUND

Volatile organic compounds (VOCs), phosphoribosylformylglycinamidine synthase, perfluorinated alkylated substances (PFAs), including perfluoroalkyl acids such as perfluorooctanoic acid (PFOA), perfluorooctane sulfonate (PFOS), hydrogen sulfide and numerous other contaminants, are unstable upon removal from their in-situ, resident location as a result of mass loss and/or cross contamination from the surrounding environment. Within an in-situ, subsurface, resident environment, these contaminants often times reach an equilibrated concentration state that depends on the temperature, pressure, pH, dissolved oxygen, oxidation reduction potential as well as other factors such as the presence of other organic and inorganic constituents. In combination, these factors define the equilibrated state in an aquifer or any other type of water bearing subsurface environment.

The volatile nature of VOCs and PFAs in solution and the losses that occur from exsolution due to changes in water chemistry and sampling conditions has been a problem faced by the environmental industry for decades. Sample concentration accuracy has been exhaustively studied and is a key focus of various litigation cases involving VOC groundwater contamination.

Unfortunately, removal of groundwater samples from their pore space environment can be accompanied by various factors that may adversely impact the sample concentration accuracy. For example, removal of groundwater samples from their pore space environment can be accompanied by factors such as (i) a decrease in hydrostatic pressure during retrieval to the surface, (ii) transferring of the sample to another container at the surface, (iii) the vapor pressure of organic molecules in solution, (iv) the proximal presence of atmospheric cross-contaminants from generators and gas powered vehicles that potentially dissolve into the groundwater sample during transfer, (v) the potential for UV degradation of the sample during transfer and within the glass sample vial itself, and (vi) the variability in terms of how the sample is handled from one field person to the next, which can all contribute to loss of volatile organic contaminants from solution and/or introduction of contaminants from the surrounding environment during the sample collection process. Even VOC degradation by microbial processes due to change in water chemistry parameters and introduction of microbes from the surface environment can be a factor. To address these concerns, some field scientists transfer water quickly from one vial to another, while others transfer water at a gentler, slower rate. Additionally, some field personnel fill the vial from the bottom using a transfer tube, while others place the transfer tube at the top of the vial and allow the water to splash and aerate into the sample container. Still other field personnel fill the vial cap with water and then quickly turn the cap over in the attempt to flood the meniscus to avoid introducing air bubbles to the inside of the vial; often times with repeated attempts to avoid introduction of air bubbles into the sample.

Conventional methods of obtaining groundwater samples for chemical analysis have not been altogether satisfactory. In obtaining representative groundwater samples for chemical analysis, current practice can require that a pump is lowered into a well or borehole (sometimes also referred to herein as a "groundwater source" or simply as a "fluid source") for the purpose of collecting a groundwater sample. When the pump reaches the required set depth, the pump can then be actuated by the operator at the ground surface.

The current procedures for how the samples are collected for VOC analysis vary when using pumps. For some projects, low flow purge and sampling methods are used. For other projects, three to five wet casing volumes are removed from the groundwater source prior to collecting a sample with the pump. Once the required volume has been purged and/or when stabilization parameters such as pH, temperature, dissolved oxygen, oxidation reduction potential, specific conductivity and turbidity are reached, the field technician can then orient the discharge from the sample return line towards the bottle(s) or sample vial(s) that need to be filled. It is during the transfer of groundwater from the pump's sample return line tube to the vial container at the ground surface where a large percentage of the dissolved VOCs are exsolved from solution due to the inherent vapor pressure of the organic molecules. Once the resident environment is breached, destabilization of the groundwater equilibrium in which the organic molecule resides begins to occur. In particular, current practice requires that a sampling device is lowered into a well or borehole, i.e. a fluid source, for the purpose of collecting a groundwater or other fluid sample. Once the apparatus is filled with the fluid, the device is then retrieved back to the surface. At the ground surface, the operator then decants the fluid sample from the sampling device and transfers the fluid into a different container in preparation for laboratory analysis. However, disturbance and degradation of the sample can occur during the retrieval of the samples to the surface as well as during the transfer to another container at the surface.

SUMMARY

The present invention is directed toward a fluid sample collection system for directly collecting a fluid sample from a fluid source without exposing the fluid sample to an ambient environment that surrounds the fluid sample collection system. In certain embodiments, the fluid source can be a borehole or a well, a lake, a pond, a river, or another suitable fluid source. In various embodiments, the fluid sample collection system includes a fluid collector including (i) a sample vial that is configured to retain fluid from the fluid source, the sample vial including a sample vial body and a vial cap that is selectively coupled and sealed to the sample vial body; (ii) a collector body that defines a passenger vial chamber, the sample vial being positioned at least partially within the passenger vial chamber during collection of the fluid; and (iii) a cap access facilitator that is configured to engage a portion of the sample vial to enable a user to selectively couple the vial cap to the sample vial body to seal the sample vial so that the fluid is retained within the sample vial.

In certain embodiments, the fluid sample collection system further includes a fluid pass-through vessel that is configured to extend through an aperture in the collector body, the fluid pass-through vessel providing a conduit through which the fluid flows from outside the collector body and into the sample vial body. In some such embodiments, the fluid enters the fluid pass-through vessel after the fluid has been removed from the fluid source, but prior to the fluid entering the sample vial body. Additionally, the fluid collector can further include a system fluid inflow conduit that is configured to be positioned within and extend through the aperture in the collector body. In such embodiments, the fluid pass-through vessel is configured to extend through the system fluid inflow conduit.

Further, in some embodiments, the fluid pass-through vessel includes a vessel distal end that is configured to be positioned near a bottom of the sample vial body.

Still further, the fluid sample collection system can further include a preservation assembly that is coupled in fluid communication to the fluid pass-through vessel, the preservation assembly being configured to selectively add a preservative to the fluid from the fluid source.

Additionally, in some embodiments, the fluid sample collection system further includes a second fluid collector that is coupled to the fluid collector, the second fluid collector including (i) a second sample vial that is configured to retain fluid from the fluid source, the second sample vial including a second sample vial body and a second vial cap that is selectively coupled and sealed to the second sample vial body; (ii) a second collector body that defines a second passenger vial chamber that is configured to selectively retain the second sample vial during collection of the fluid; and (iii) a second cap access facilitator that is configured to engage a portion of the second sample vial to enable a user to selectively couple the second vial cap to the second sample vial body to seal the second sample vial so that the fluid is retained within the second sample vial.

In such embodiments, the fluid sample collection system can further include a distribution system that receives fluid from the fluid source, the distribution system being configured to distribute fluid to each of the fluid collector and the second fluid collector.

In certain embodiments, the fluid sample collection system further includes a fluid parameter testing system that is configured to receive excess fluid from the fluid collector. The fluid parameter testing system includes a sensor that is configured to sense at least one fluid parameter of the excess fluid that is received from the fluid collector.

Additionally, in some embodiments, the fluid sample collection system further includes a pump assembly that pumps the fluid out of the fluid source and directs the fluid to the fluid collector. It is appreciated, however, that the fluid can be moved from the fluid source to the fluid collector in another suitable manner, i.e. other than through the use of a pump assembly.

In certain embodiments, the passenger vial chamber is configured to selectively retain a plurality of sample vials simultaneously. Additionally, in some embodiments, the passenger vial chamber is formed from a non-rigid material.

Additionally, in certain embodiments, the collector body further defines an antechamber that is positioned substantially adjacent to the passenger vial chamber. The antechamber is configured to provide access to the cap access facilitator for the user. Further, in such embodiments, the antechamber is not in fluid communication with the passenger vial chamber.

In some embodiments, the sample vial further includes a cap holder that is coupled to the vial cap. In certain such embodiments, the cap access facilitator is configured to selectively engage and retain the cap holder during selective coupling between the vial cap and the sample vial body.

Further, in various embodiments, the collector body includes a vial aperture, and the sample vial is moved into and out of the passenger vial chamber through the vial aperture. In such embodiments, the fluid collector can further include a vial aperture seal that seals a connection between the sample vial and the collector body adjacent to the vial aperture when the sample vial is positioned at least partially within the passenger vial chamber.

The present invention is also directed toward a method for directly collecting a fluid sample from a fluid source without exposing the fluid sample to an ambient environment, the method including the steps of providing a fluid collector that includes a collector body that defines a passenger vial chamber; positioning a sample vial at least partially within the passenger vial chamber, the sample vial including a sample vial body and a vial cap that is selectively coupled and sealed to the sample vial body; receiving and retaining fluid from the fluid source within the sample vial body; and engaging a portion of the sample vial with a cap access facilitator to selectively couple the vial cap to the sample vial body to seal the sample vial so that the fluid is retained within the sample vial.

Additionally, in certain applications, the present invention is further directed toward a fluid sample collection system including (A) a fluid collector including (i) a sample vial that is configured to retain fluid from the fluid source, the sample vial including a sample vial body and a vial cap that is selectively coupled and sealed to the sample vial body; (ii) a collector body that defines a passenger vial chamber, the sample vial being positioned at least partially within the passenger vial chamber during collection of the fluid; and (iii) a cap access facilitator that is configured to engage a portion of the sample vial to enable a user to selectively couple the vial cap to the sample vial body to seal the sample vial so that the fluid is retained within the sample vial; (B) a pump assembly that pumps the fluid out of the fluid source and directs the fluid to the fluid collector; (C) a system fluid inflow conduit that is configured to be positioned within and extend through an aperture in the collector body; (D) a fluid pass-through vessel that is configured to extend through the system fluid inflow conduit, the fluid pass-through vessel providing a conduit through which the fluid flows from outside the collector body and into the sample vial body, the fluid entering the fluid pass-through vessel after the fluid has been removed from the fluid source, but prior to the fluid entering the sample vial body; and (E) a fluid parameter testing system that is configured to receive excess fluid from the fluid collector, the fluid parameter testing system including a sensor that is configured to sense at least one fluid parameter of the excess fluid that is received from the fluid collector.

Further, the present invention is also directed toward a fluid sample collection system including (A) a fluid collector including (i) a sample vial that is configured to retain preserved fluid from the raw fluid source, the sample vial including a sample vial body and a vial cap that is selectively coupled and sealed to the sample vial body; (ii) a collector body that defines a passenger vial chamber, the sample vial being positioned at least partially within the passenger vial chamber during collection of the fluid; and (iii) a cap access facilitator that is configured to engage a portion of the sample vial to enable a user to selectively couple the vial cap to the sample vial body to seal the sample vial so that the fluid is retained within the sample vial; (B) a fluid mover that moves the raw fluid from the raw fluid source toward the fluid collector; (C) a system fluid inflow conduit that is configured to be positioned within and extend through an aperture in the collector body; (D) a fluid pass-through vessel that is configured to extend through the system fluid inflow conduit, the fluid pass-through vessel providing a conduit through which the fluid flows from outside the collector body and into the sample vial body, the fluid entering the fluid pass-through vessel after the fluid has been removed from the fluid source, but prior to the fluid entering the sample vial body; and (E) a preservative assembly that is in fluid communication with the fluid pass-through vessel, the preservative assembly being configured to selectively add preservative material to raw fluid from the raw fluid source to provide the preserved fluid.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters can refer to similar parts, and in which:

FIG. 5A is a simplified schematic view illustration of another embodiment of the sample vial assembly and another embodiment of a portion of the cap access facilitator that is shown prior to engagement with a sample vial;

FIG. 5B is a simplified schematic illustration of the sample vial assembly and the portion of the cap access facilitator illustrated in FIG. 5A, with the cap access facilitator shown engaging the sample vial.

DESCRIPTION

Embodiments of the present invention are described herein in the context of a fluid sample collection system (sometimes referred to herein as a "collection system") and method for collecting fluid samples that have been removed from, e.g., pumped from, a fluid source. More particularly, the embodiments of the collection system and method described in detail herein help to provide much greater consistency during the collection of fluid samples, while inhibiting exposure of the fluid samples to undesired environmental influences. Thus, the embodiments of the collection system and method are able to provide greatly improved accuracy when evaluating the true level of contaminants within the fluid source.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same or similar nomenclature and/or reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1A:
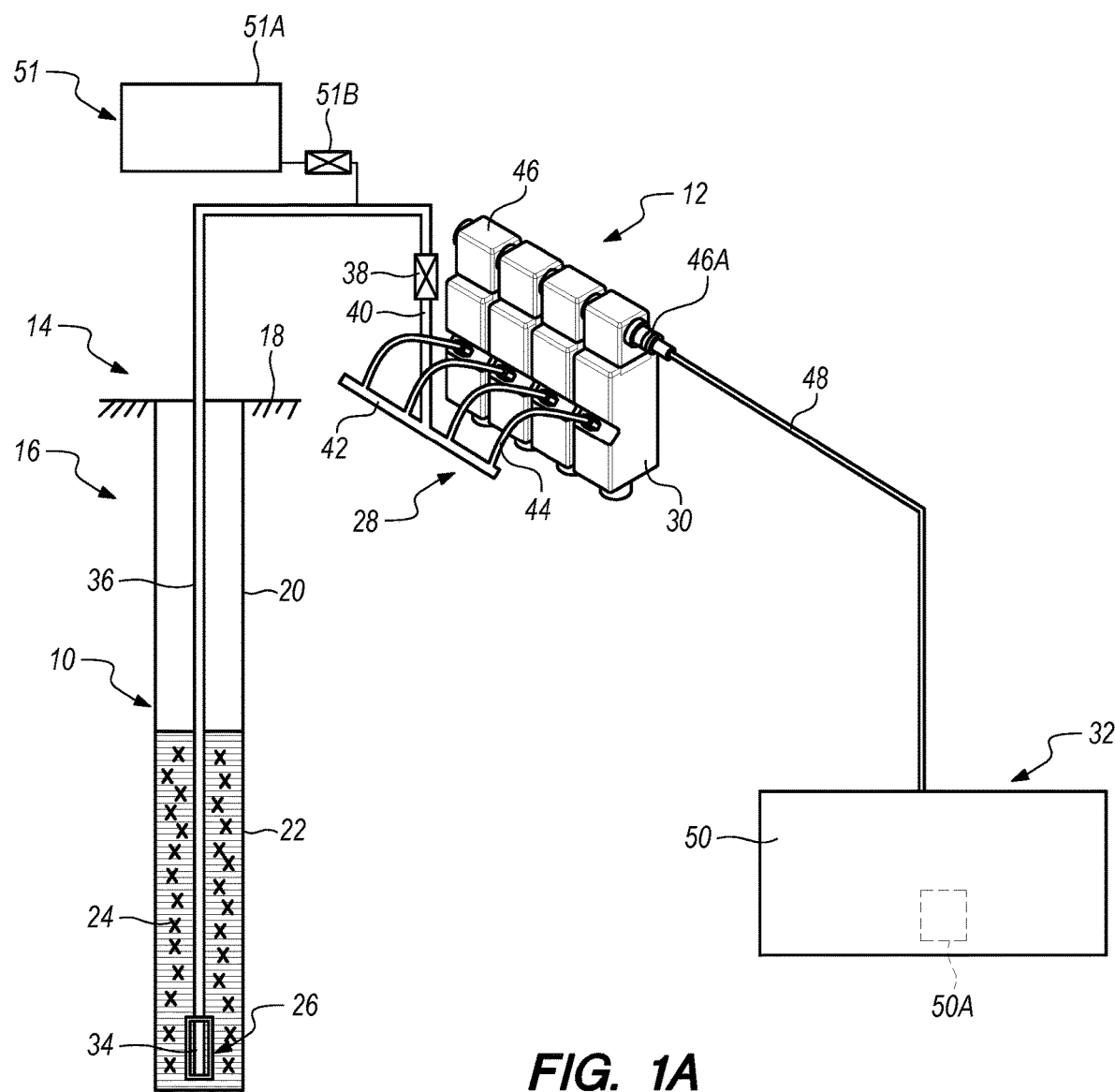
FIG. 1A is a simplified schematic view illustration of a fluid source and an embodiment of a fluid sample collection system having features of the present invention that is positioned primarily outside of the fluid source.

FIG. 1A is a simplified schematic view illustration of a fluid source 10, e.g., a groundwater production well or borehole in this particular application, and an embodiment of a fluid sample collection system 12 having features of the present invention that is positioned primarily outside of the fluid source 10.

It is appreciated that although the collection system 12 and method disclosed herein is primarily illustrated and described for use with a groundwater well or borehole, the collection system 12 and method is equally usable with any type of fluid source 10. For example, in addition to being usable in conjunction with a groundwater well or borehole, the collection system 12 and method can also be used to collect fluid samples from another type of fluid well, a lake, a pond, a river, a barrel, a tank, a pressure vessel, a canister, a container, a funnel, or any other suitable fluid source. Thus, the specific discussions herein of use of the collection system 12 and method in conjunction with a groundwater well or borehole is not intended to be limiting in any manner.

Additionally, it is further appreciated that embodiments of the collection system 12 as described herein can be used for various industrial applications, e.g., pharmacology, laboratory, beverages, etc., in addition to the noted use for collecting fluid samples for testing environmental conditions of fluid resources.

The well fluid source 10 can be installed using any one of a number of methods known to those skilled in the art. In non-exclusive, alternative examples, the fluid source 10 can be installed with hollow stem auger, sonic, air rotary casing hammer, dual wall percussion, dual tube, rotary drilling, vibratory direct push, cone penetrometer, cryogenic, ultrasonic and laser methods, or any other suitable method known to those skilled in the art of drilling and/or well placement.

As illustrated, the fluid source 10 can be said to include a surface region 14 and a subsurface region 16. The surface region 14 is an area that extends to and/or is positioned above a surface 18. The surface 18 can either be a ground surface or the surface of a body of water or other liquid, as non-exclusive examples. The subsurface region 16 is the portion of the fluid source 10 that is below the surface 18 and below the surface region 14, e.g., at a greater depth than the surface region 14.

Additionally, as illustrated, the fluid source 10 includes a support casing 20 and a well screen 22. The support casing 20 can be a hollow, generally cylinder-shaped structure that extends in a generally downward direction into the subsurface region 16 to help provide access to a fluid 24 (illustrated as a plurality of "x"s in FIG. 1A, e.g., groundwater or other fluids, present within the subsurface region 16. The support casing 20 can have any desired thickness and can be formed from materials such as polyvinylchloride (PVC), other plastics, fiberglass, ceramics, metal, or other suitable materials. Additionally, the length of the support casing 20 can be varied to suit the specific design requirements of the fluid source 10 and/or depending on the specific locations of the desired fluid 24 within the subsurface region 16. Further, an inner diameter of the support casing 20 can vary depending upon the specific design requirements of the fluid source 10. It is understood that although the support casing 20 is illustrated in FIG. 1A as being positioned substantially vertically, the support casing 20 and the other structures of the fluid source 10 can alternatively be positioned at any suitable angle relative to vertical.

The well screen 22 extends from and/or forms a portion of the support casing 20 within the subsurface region 16. The well screen 22 can comprise a perforated pipe that provides an access means through which the fluid 24 enters the fluid source 10. As illustrated, the well screen 22 is adapted to be positioned at a level within the subsurface region 16 in vertical alignment with and/or substantially adjacent to the fluid 24 within the subsurface region 16. It is noted that although the well screen 22 is shown as extending in a substantially continuous manner adjacent to the fluid 24 within the subsurface region 16; the well screen 22 can alternatively be positioned in a more discretized manner, such that the well screen 22 is provided in a number of individual sections that are positioned only in vertical alignment with and/or substantially adjacent to certain portions of the fluid 24.

The design of the collection system 12 can be varied depending on the specific requirements and characteristics of the fluid source 10, and/or depending on the specific availability of the fluid 24, e.g., groundwater or other fluid, within the subsurface region 16. In various embodiments, as shown in FIG. 1A, the collection system 12 includes a pump assembly 26, a fluid distribution system 28 (sometimes referred to herein simply as a "distribution system"), at least one fluid collector 30, and a fluid parameter testing system 32 (sometimes referred to herein simply as a "parameter testing system"). As illustrated in this embodiment, each of the distribution system 28, the at least one fluid collector 30 and the parameter testing system 32 are positioned outside of the fluid source 10 during collection of the fluid 24 from the fluid source 10. Alternatively, the collection system 12 can include more components or fewer components than those specifically illustrated in FIG. 1A. For example, in certain non-exclusive alternative embodiments, the collection system 12 can be designed without the parameter testing system 32. In still other non-exclusive alternative embodiments, where the collection system 12 only includes a single fluid collector 30, the collection system 12 need not include the distribution system 28.

As an overview, the collection system 12 is configured to collect one or more fluid samples 24S (illustrated as a plurality of "x"s in FIG. 2E) from the fluid source 10 for purposes of testing and evaluating the true level of contaminants within the fluid source 10. In particular, the design of the collection system 12 enables the collection of such fluid samples 24S from the fluid source 10 in a manner that inhibits contact of the fluid sample 24S with the ambient environment (or atmosphere) that surrounds the collection system 12. With such design, the collection system 12 is able to achieve certain significant objectives, including, but not limited to: (1) prevention of loss or reaction to the ambient environment of volatile species within the fluid sample 24S; (2) exclusion of sample contaminants that may be present in the ambient environment surrounding the fluid collectors 30; (3) enforcement of consistency of physical practice in the sampling method; and (4) reducing standard deviation in sample results by enforcing consistency.

The pump assembly 26 provides a means to selectively remove the fluid 24 from the fluid source 10 to be collected as the desired fluid samples 24S. The design of the pump assembly 26 can be varied. As illustrated in FIG. 1A, the pump assembly 26 can include a pump 34, and a fluid return line 36. Alternatively, the pump assembly 26 can have a different design.

The collection system 12 can utilize any suitable type of pump 34 for purposes of pumping the fluid 24 out of the fluid source 10, i.e. to provide the desired fluid samples 24S. For example, in certain non-exclusive alternative embodiments, the pump 34 can be a line shaft turbine or electric submersible pump, a bladder pump, a variable frequency drive centrifugal submersible pump, a single valve parallel gas displacement pump, double valve pump, a progressive cavity pump, a piston pump (single-action or double-action), or a gear-driven pump. Alternatively, the pump 34 can be another suitable type of pump.

The fluid return line 36 is coupled to the pump 34, and provides a conduit through which the fluid 24 that will comprise the fluid samples 24S are moved from the fluid source 10 to the fluid distribution system 28 and/or the fluid collectors 30 without the fluid 24 being exposed to the ambient environment. Stated in another manner, the pump 34 and the fluid distribution system 28 and/or the fluid collectors 30 are in fluid communication via the fluid return line 36. The fluid return line 36 can have any suitable design. For example, in certain non-exclusive embodiments, the fluid return line 36 can include a flexible tube that is coupled to and extends between the pump 34 and the distribution system 28 and/or the fluid collectors 30.

Because the collection system 12 is generally described as being usable for collecting fluid samples 24S from a fluid source 10 using a pump assembly 26, the pump assembly 26 is generally considered to be a part of the collection system 12. However, as the collection system 12 may also be usable to collect fluid samples 24S from a fluid source 10 without the specific use of a pump, the collection system 12 need not include the pump in order for proper operation of the collection system 12. For example, in one non-exclusive alternative embodiment, the fluid 24 from the fluid source 10 can be moved to the distribution system 28 and/or the fluid collectors 30 via gravity feed from a tube in a manner that also inhibits contact of the fluid 24 with the ambient environment. Still alternatively, movement of the fluid 24 from the fluid source 10 can utilize other methods such as tapping into a pressurized pipeline, vessel or municipal tap. As such, the pump assembly 26 or other suitable assembly for moving the fluid 24 from the fluid source 10 to the distribution system 28 and/or the fluid collectors 30 can also referred to as a "fluid mover".

The distribution system 28 receives the fluid samples 24S from the fluid return line 36 of the pump assembly 26, and distributes the fluid samples 24S to each of the fluid collectors 30. The design of the distribution system 28 can be varied to suit the requirements of the collection system 12. As illustrated in the embodiment shown in FIG. 1A, the distribution system 28 includes a connector valve 38, a distributor inlet 40, a distribution line 42, and at least one collector inlet line 44. Alternatively, the distribution system 28 can include additional components or fewer components than those specifically illustrated and described herein.

The connector valve 38 provides the desired connection between the fluid return line 36 and the distributor inlet 40. In certain embodiments, the connector valve 38 can be a one-way valve that selectively permits the fluid 24 from the fluid source 10, e.g., the fluid samples 24S, to flow from the fluid return line 36 into the distributor inlet 40. By utilizing a one-way valve, the fluid samples 24S are inhibited from flowing from the distribution system 28 back into the fluid return line 36. Additionally, as provided herein, when it is determined that sufficient fluid 24 has been collected with the collection system 12, i.e. into the fluid collectors 30, to comprise the desired fluid samples 24S, the connector valve 38 can then be closed to inhibit additional fluid 24 from entering into the distribution system 28.

The distributor inlet 40 is a conduit through which the fluid 24 traverses from the fluid return line 36 to the distribution line 42. The distribution line 42 then functions as a manifold to distribute the fluid 24 to each of the at least one collector inlet lines 44. For example, in the embodiment illustrated in FIG. 1A, the distribution line 42 distributes the fluid 24 to each of four collector inlet lines 44, with each collector inlet line 44 being coupled to a separate fluid collector 30. Alternatively, the distribution system 28 can include greater than four or fewer than four collector inlet lines 44 depending on the number of fluid collectors 30 that are included within the collection system 12. For example, in certain non-exclusive alternative embodiments, the distribution system 28 can be configured to include one, two, three, five or six collector inlet lines 44, when the collection system includes one, two, three, five or six fluid collectors 30, respectively. The distributing or splitting of the fluid 24 among multiple collectors 30 enables the collection system 12 to collect multiple fluid samples 24S substantially simultaneously.

It is appreciated that, as noted above, in embodiments that include only a single fluid collector 30, the collection system 12 can be designed without the distribution system 28, and the fluid return line 36 can be coupled substantially directly to the fluid collector 30.

The fluid collectors 30 are configured to receive and retain the desired number of fluid samples 24S from the fluid source 10. In the embodiment shown in FIG. 1A, the collection system 12 includes four fluid collectors 30, with each fluid collector 30 being configured to collect a single fluid sample 24S at any given time. Alternatively, the collection system 12 can include greater than four or fewer than four fluid collectors 30. Still alternatively, in other embodiments, any fluid collector 30 can be configured to collect more than one fluid sample 24S at any given time, i.e. substantially simultaneously. The specific design and functionality of embodiments of the fluid collectors 30 will be described in greater detail herein below.

As provided herein, the fluid parameter testing system 32 is configured to receive some of the fluid 24 from the fluid source 10 during collection of the desired fluid samples 24S. Additionally, the fluid parameter testing system 32 is further configured to ensure stabilization within the parameters of the fluid samples 24S, so as to further ensure that the fluid samples 24S accurately reflect the true makeup of the fluid source 10, e.g., the true level of contaminants within the fluid 24 found in the fluid source 10. The design of the parameter testing system 32 can be varied to suit the requirements of the collection system 12. In certain embodiments, as shown, the parameter testing system 32 includes a fluid parameter testing facilitator 46, a fluid testing line 48, and a parameter testing cell 50. Alternatively, the parameter testing system 32 can include additional components or fewer components than those specifically illustrated and described herein.

The fluid parameter testing facilitator 46 is configured to receive portions of the fluid 24 that have flowed through and out of each of the fluid collectors 30. Subsequently, the fluid parameter testing facilitator 46 combines such excess fluid from each of the fluid collectors 30 and directs the excess fluid toward the parameter testing cell 50 via a flow valve 46A and the fluid testing line 48. Stated in another manner, the fluid parameter testing facilitator 46 is in fluid communication with each of the fluid collectors 30 and with the parameter testing cell 50. It is appreciated that the fluid parameter testing facilitator 46 can function in substantially the same manner regardless of the number of fluid collectors 30 that may be present within the collection system 12, e.g., even if the collection system 12 only includes a single fluid collector 30.

The parameter testing cell 50 then tests one or more parameters of the excess fluid to ensure stabilization of the one or more parameters, and thus stabilization of the fluid samples 24S that are being collected from the fluid source 10. In some embodiments, the parameter testing cell 50 can include at least one sensor 50A (illustrated as a box in phantom) for sensing and testing the one or more fluid parameters of the fluid 24. For example, in certain such embodiments, the at least one sensor 50A can be configured to sense such fluid parameters as pH, temperature, conductivity, dissolved oxygen, oxidation reduction potential, and turbidity, as well as the presence or absence of any particular chemicals.

As noted, when the levels of such fluid parameters have become stabilized, i.e. the levels are not changing over time other than acceptable mild variations, it is appreciated that the fluid samples 24S can then be accepted as a true and accurate representation of the actual component, e.g., including chemical and/or contaminant components, makeup of the fluid 24 from the fluid source 10. Additionally, once such parameter stabilization has been achieved, the fluid samples 24S can then be sealed within an appropriate portion of the fluid collectors 30 and sent for any suitable and desired laboratory testing of such fluid samples 24S.

It is appreciated that, although the fluid parameter testing system 32 is illustrated in FIG. 1A as being coupled to an outflow portion of the collection system 12, i.e. after the fluid 24 has flowed into and through the fluid collectors 30, the fluid parameter testing system 32 can be alternatively coupled to an inflow portion of the collection system 12, i.e. before the fluid 24 has flowed into and through the fluid collectors 30.

As shown in FIG. 1A, in some embodiments, the collection system 12 can further include a preservation assembly 51 that may be included to selectively add preservatives to the fluid 24 to help preserve the integrity of the fluid samples 24S that are being collected from the fluid source 10 and/or to extend the amount of time that the fluid samples 24S can be held prior to laboratory analysis. More specifically, in such embodiments, the preservative can be added for various purposes including, but not limited to preservation, reaction, sterilization, or other physical or chemical interaction. For example, in such embodiments, the preservation assembly 51 can include a preservative reservoir 51A that retains preservatives, and that is in fluid communication with the fluid return line 36. The preservative can be provided in fluid form, particulate form, or another suitable form. Additionally, control of preservatives from the preservative reservoir 51A into the fluid return line 36 can be controlled with a preservative valve 51B. Further, or in the alternative, flow of preservatives from the preservative reservoir 51A can be controlled and/or supplied by an active pumping mechanism, by gravity feed, or by a syringe or other pressure differential device.

In such embodiments, the fluid 24 from the fluid source 10 can be referred to as a "raw fluid" from a "raw fluid source"; and the fluid with the preservative having been added thereto can be referred to as a "preserved fluid".

Additionally, as further illustrated in FIG. 1A, the combined flow of the fluid 24 from the fluid source 10 and the preservative from the preservation assembly 51 can be controlled by the connector valve 38 of the distribution system 28. Further, as noted, the distributor inlet 40, the distribution line 42 (i.e. manifold), and collector inlet lines 44 can be used to split the combined flow of fluid 24 and preservative among the multiple collectors 30 to provide for the substantially simultaneous collection of multiple fluid samples 24S.

It is appreciated that although the preservative assembly 51 is shown as being coupled to the fluid return line 36 between the pump 34 and the distribution system 28, the preservative assembly 51 can alternatively be coupled to a different portion of the collection system 12. For example, in one non-exclusive alternative embodiment, the preservative assembly 51 can be coupled to the collection system 12 within the distribution system 28, e.g., can be coupled to the distributor inlet 40, the distribution line 42 and/or the collector inlet lines 44. Additionally, it is further appreciated that preservatives from the preservative reservoir 51A can be added during or after the collection of the fluid 24 from the fluid source 10.

Additionally, in certain embodiments, a portion of the collection system 12, e.g., the fluid collectors 30, can be supported by a device stand (not shown), e.g., a rack, a tripod, or the like) to inhibit the fluid collectors 30 from tipping over as well as to raise the fluid collectors 30 above a working surface so as not to allow surficial contact with the working surface to avoid being influenced by the surface temperature.

Figure 1B:
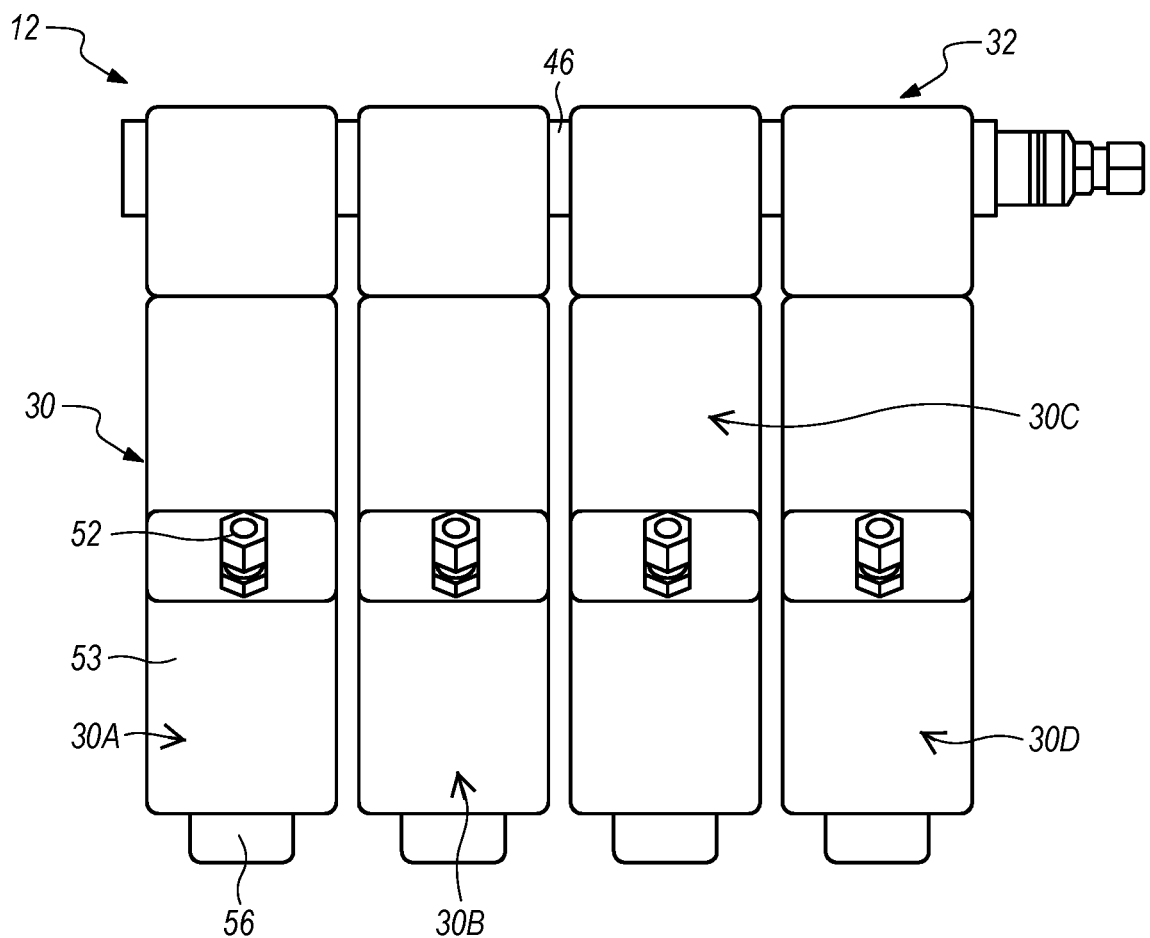
FIG. 1B is a simplified schematic view illustration of a portion of the fluid sample collection system illustrated in FIG. 1A.

FIG. 1B is a simplified schematic view illustration of a portion of the fluid sample collection system 12 illustrated in FIG. 1A. In particular, FIG. 1B is a simplified schematic illustration of four fluid collectors 30, i.e. a first fluid collector 30A, a second fluid collector 30B, a third fluid collector 30C and a fourth fluid collector 30D, that are coupled together, and that are further coupled to the fluid parameter testing facilitator 46 of the parameter testing system 32.

As shown in FIG. 1B, each fluid collector 30A-30B includes a system fluid inflow conduit 52, a collector body 53, and a sample vial assembly 56.

The system fluid inflow conduit 52 provides an access point through which the fluid 24 (illustrated in FIG. 1A) passes from the collector inlet line 44 (illustrated in FIG. 1A) of the distribution system 28 (illustrated in FIG. 1A) into the collector body 53. More specifically, in certain embodiments, the collector inlet line 44 can extend through the system fluid inflow conduit 52 into the collector body 53.

The collector body 53 is configured to provide a housing around at least a portion of the sample vial assembly 56 during use of the collection system 12. In particular, in the position shown in FIG. 1B, for each fluid collector 30A-30D, only a fairly small portion of the sample vial assembly 56 extends below and/or outside the general confines of the collector body 53.

The various features of embodiments of the fluid collector 30 will be described in greater detail herein below.

Figure 2A:
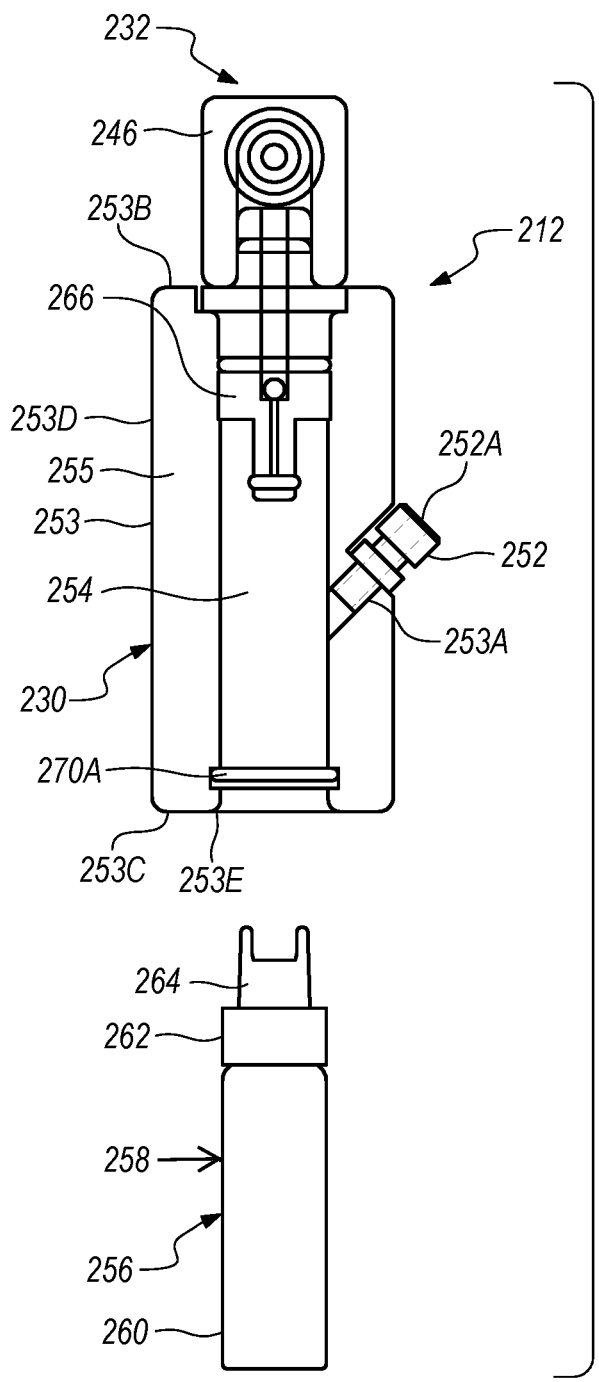
FIG. 2A is a partially exploded schematic view illustration of a portion of one embodiment of the fluid sample collection system, the fluid sample collection system including a fluid collector having a passenger vial chamber and a sample vial assembly that is shown in a first position relative to the passenger vial chamber.

FIG. 2A is a partially exploded schematic view illustration of a portion of one embodiment of the fluid sample collection system 212. In particular, FIG. 2A illustrates an embodiment of a fluid collector 230 that can be used within the collection system 212. The design of the fluid collector 230 can be varied to suit the requirements of the fluid source 10 (illustrated in FIG. 1) with which the collection system 212 is being used. In various embodiments, as shown in FIG. 2A, the fluid collector 230 includes (i) a system fluid inflow conduit 252 (also sometimes referred to herein simply as an "inflow conduit"), (ii) a collector body 253 that defines and/or includes a passenger vial chamber 254 and an antechamber 255, (iii) a sample vial assembly 256 including at least one sample vial 258 having a sample vial body 260, a vial cap 262 and a cap holder 264, and (iv) a cap access facilitator 266. As illustrated, the sample vial 258 is shown in a first position relative to the collector body 253 and/or the passenger vial chamber 254, i.e. with the sample vial 258 positioned completely outside the collector body 253 and completely outside the passenger vial chamber 254. Additionally, or in the alternative, the fluid collector 230 can include more components or fewer components than those specifically illustrated and described herein.

FIG. 2A further illustrates a portion of the fluid parameter testing system 232, i.e. the fluid parameter testing facilitator 246, that can be included as part of the collection system 212.

The inflow conduit 252 provides an access point through which the fluid 24 (illustrated in FIG. 1A) from the fluid source 10 (illustrated in FIG. 1A) passes into the collector body 253 and/or the passenger vial chamber 254. The design of the inflow conduit 252 can be varied to suit the requirements of the collection system 212. In certain embodiments, the inflow conduit 252 can be a sealable plug that is configured to selectively fit within and extend through a fluid aperture 253A that extends through the collector body 253 and into the passenger vial chamber 254. Additionally, the inflow conduit 252 can be configured to receive a fluid pass-through vessel 268 (illustrated in FIG. 2E) through which the fluid 24 flows prior to the fluid 24 entering the sample vial 258, i.e. the sample vial body 260. More particularly, as shown, the inflow conduit 252 includes a conduit aperture 252A through which the fluid pass-through vessel 268 can extend to enable the fluid 24 to flow from outside the collector body 253 to inside the collector body 253 and/or the passenger vial chamber 254 without the fluid 24 being adversely impacted by the ambient environment.

As above, the collector body 253 is configured to provide a housing around at least a portion of the sample vial assembly 256. Additionally, in this embodiment, the collector body 253 defines and/or includes the passenger vial chamber 254 and the antechamber 255 that is positioned substantially adjacent to the passenger vial chamber 254 and/or substantially encircles the passenger vial chamber 254.

As shown in FIG. 2A, the collector body 253 is substantially rectangular box-shaped and includes a top 253B, a base 253C, a plurality of sides 253D, the fluid aperture 253A and a vial aperture 253E. Alternatively, the collector body 253 can have another suitable design and/or be another suitable shape, e.g., substantially cylinder-shaped.

Additionally, the collector body 253 can be made of any suitable materials. For example, in certain embodiments, the collector body 253 can be made from one or more of any type of plastic, steel, fiberglass, composites or any other suitable material.

In the embodiment shown in FIG. 2A, the sample vial assembly 256 is configured to fit, at least in part, within the passenger vial chamber 254 that is formed into the collector body 253. The design of the passenger vial chamber 254 can be varied. As shown in the embodiment illustrated in FIG. 2A, the passenger vial chamber 254 can be substantially cylinder-shaped and can be configured to receive one sample vial 258 at least partially therein. Alternatively, the passenger vial chamber 254 can be configured to receive more than one sample vial 258 at least partially therein.

Additionally, in certain embodiments, the passenger vial chamber 254 can be formed from a non-rigid material, such that a flexible container is provided around the sample vial 258. Alternatively, in other embodiments, the passenger vial chamber 254 can be formed from a more rigid material.

Further, as provided herein, the passenger vial chamber 254 can be configured to allow the fluid 24 to flow into, through, and out of the passenger vial chamber 254 during collection of the fluid samples 24S.

The fluid aperture 253A and the vial aperture 253E can be positioned in any suitable manner about the collector body 253. In this embodiment, the fluid aperture 253A is configured to extend, at an angle, through one of the sides 253D of the collector body 253. Alternatively, in other embodiments, the fluid aperture 253A can extend through the top 253B or the base 253C of the collector body 253.

Figure 2B:
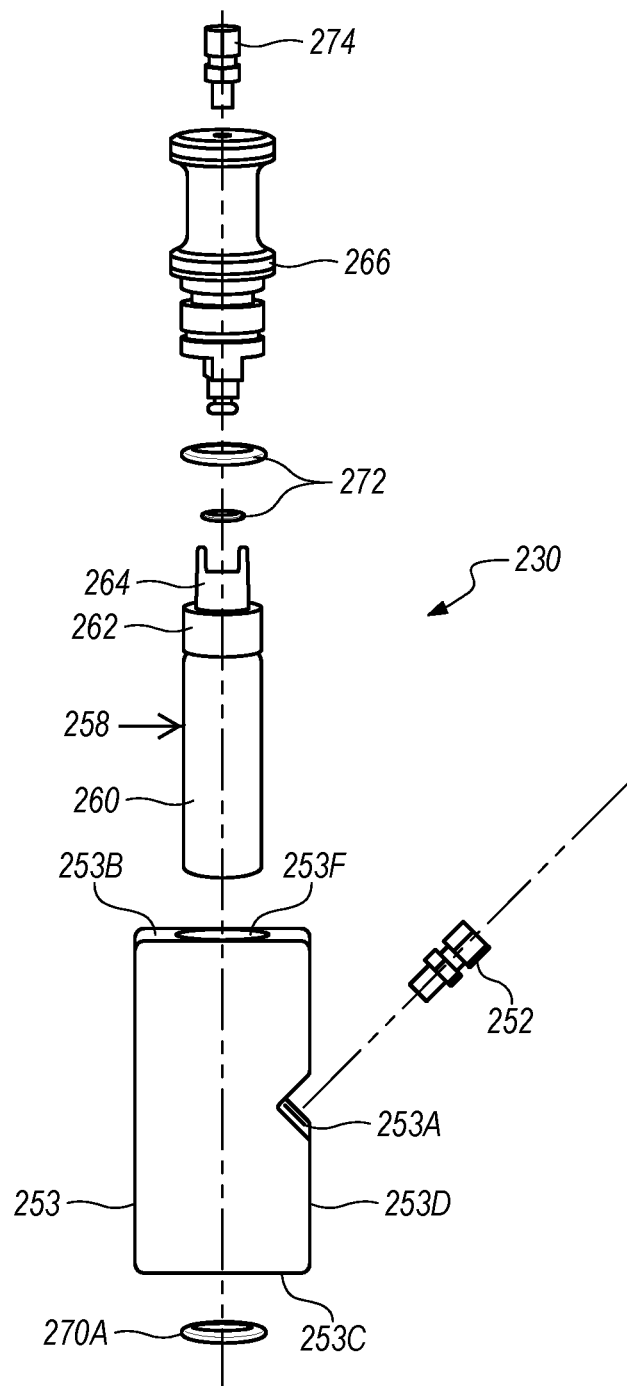
FIG. 2B is an exploded view illustration of the fluid collector illustrated in FIG. 2A.
Figure 2C:
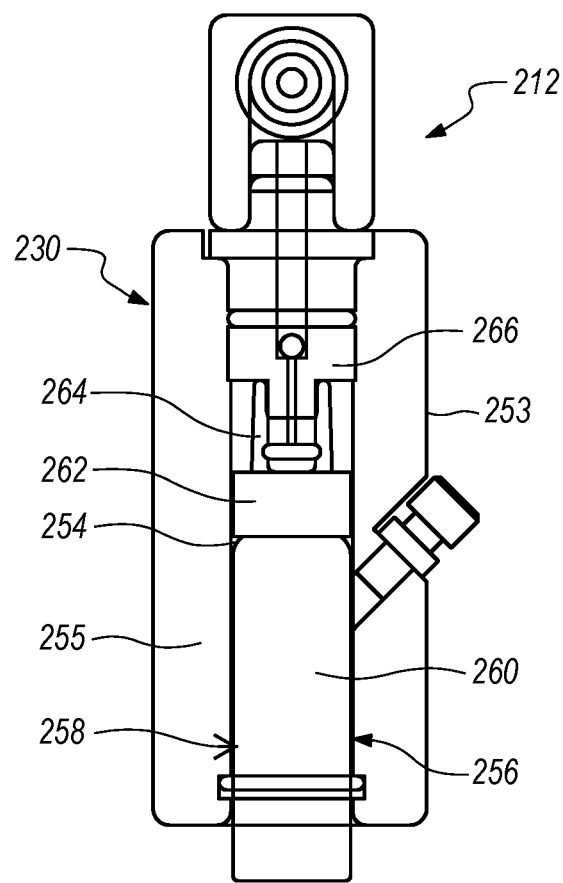
FIG. 2C is a simplified schematic front view illustration of the portion of the fluid sample collection system illustrated in FIG. 2A, the sample vial assembly being shown in a second position relative to the passenger vial chamber.

The vial aperture 253E provides access for the sample vial 258 to move between the first position, where the sample vial 258 is positioned outside the collector body 253 (as shown in FIG. 2A), and a second position, where the sample vial 258 is positioned substantially within an interior of the collector body 253 (as shown in FIG. 2C). More specifically, the vial aperture 253E provides access for the sample vial 258 into and out of the passenger vial chamber 254. In one embodiment, the vial aperture 253E can be configured to extend through the base 253C of the collector body 253. With this design, the sample vial 258 can be moved in a generally upward direction through the vial aperture 253E as the sample vial 258 is moved from the first position to the second position. Alternatively, in other embodiments, the vial aperture 253E can be configured to extend through another portion of the collector body 253, i.e. through the top 253B or one of the sides 253D of the collector body 253.

FIG. 2A further illustrates a vial aperture seal 270A, e.g., an O-ring, that can seal the vial aperture 253E about the sample vial 258 when the sample vial 258 is positioned at least partially within the collector body 253, i.e. at least partially within the passenger vial chamber 254. The vial aperture seal 270A provides a friction-type fit between the sample vial 258 and the collector body 253 so as to effectively hold the sample vial 258 at least partially within the passenger vial chamber 254 of the collector body 253. Further, as provided herein, the vial aperture seal 270A is configured to seal the connection between the sample vial 258 and the body chamber 254B within the vial aperture 254F to seal the environment within the antechamber 255, i.e. between the passenger vial chamber 254 and the top 253B, base 253C and sides 253D of the collector body 253. As such, the vial aperture seal 270A can inhibit ambient environmental factors from contacting and potentially adversely impacting (i.e. changing the component make-up of) the fluid 24 that is contained within the collector body 253 and/or within the sample vial 258.

As provided herein, the antechamber 255 is a chamber that is provided within the collector body 253 and substantially adjacent to the passenger vial chamber 254. In some embodiments, as shown, the antechamber 255 is a chamber that is provided between the passenger vial chamber 254 and the top 253B, base 253C and sides 253D of the collector body 253. In certain embodiments, the antechamber 255 can assist in the process of remotely closing and opening the sample vial 258 when the sample vial 258 is positioned within the passenger vial chamber 254 without substantially exposing the sample vial 258 to the external atmosphere surrounding the collection system 212. For example, in some such embodiments, the antechamber 255 can help provide access to the cap access facilitator 266 and/or the sample vial 258 (i.e. when the sample vial 258 is positioned at least partially within the passenger vial chamber 254).

As noted above, in certain embodiments, the sample vial 258 includes the sample vial body 260, the vial cap 262, and the cap holder 264. The sample vial body 260 and the vial cap 262 can be selectively coupled to one another to form a selectively sealed container in which the fluid samples 24S (illustrated in FIG. 2E) can be collected for desired testing. In some embodiments, the vial cap 262 can be simply screwed onto and off of the sample vial body 260. Alternatively, the vial cap 262 can be coupled to the sample vial body 260 in a different manner.

The cap holder 264 provides a means for facilitating the selectively coupling between the vial cap 262 and the sample vial body 260 when such coupling, or uncoupling occurs within the collector body 253 and/or within the passenger vial chamber 254. In particular, in some embodiments, the cap holder 264 can be selectively engaged by the cap access facilitator 266 for purposes of facilitating the selective coupling or uncoupling of the vial cap 262 and the sample vial body 260. For example, in certain such embodiments, the cap access facilitator 266 can engage the cap holder 264 so as to hold the cap holder 264 and thus the vial cap 262 in position as the sample vial body 260 is coupled to or uncoupled from the vial cap 262.

In the embodiment shown in FIG. 2A, the cap access facilitator 266 extends in a generally downward direction from the top 253B of the collector body 253 and into an interior of the collector body 253. More specifically, in such embodiment, the cap access facilitator 266 can extend in a generally downward direction into an upper portion of the passenger vial chamber 254. In some embodiments, the cap access facilitator 266 is selectively fixed in position as shown within the interior of the chamber body 254B. As such, the cap access facilitator 266 can easily engage the cap holder 264 of the sample vial 258 when the sample vial 258 has been moved from the first position to the second position. In addition to providing a hand grip for the cap holder 264, the cap access facilitator 266 can further be configured to provide a travel stop to ensure the correct positioning of the cap holder 264 within the collector body 253. As provided herein, the cap access facilitator 266 may be further configured to facilitate the transfer of fluid 24 out of the collector body 253, e.g., to facilitate movement of the fluid 24 to the fluid parameter testing system 232, or to another apparatus or process or part of the process stream, as desired.

It is appreciated that in some embodiments, the antechamber 255 can provide additional access to the cap access facilitator 266 for means of ensuring that the cap access facilitator 266 is maintained in the desired position during the selective coupling and uncoupling of the vial cap 262 and the sample vial body 260 while the sample vial 258 is positioned, at least in part, within the passenger vial chamber 254.

FIG. 2B is an exploded view illustration of the fluid collector 230 illustrated in FIG. 2A. In particular, FIG. 2B illustrates the inflow conduit 252, the collector body 253, the sample vial 258 having the sample vial body 260, the vial cap 262 and the cap holder 264, and the cap access facilitator 266, and certain additional features and components of the fluid collector 230.

As shown in FIG. 2B, the inflow conduit 252 can be configured to extend through the fluid aperture 253A in the collector body 253 to provide a sealed access point through which the fluid 24 (illustrated in FIG. 1A) from the fluid source 10 (illustrated in FIG. 1A) passes into the collector body 253 and/or into the passenger vial chamber 254 (illustrated in FIG. 2A).

Additionally, FIG. 2B further illustrates that the collector body 253 can further include a facilitator aperture 253F through which the cap access facilitator 266 can be positioned to extend within the interior of the collector body 253. As shown in this embodiment, the facilitator aperture 253F can be formed in the top 253B of the collector body 253. Alternatively, the facilitator aperture 253F can be formed in another part of the collector body 253, e.g., the base 253C or one of the sides 253D of the collector body 253.

Further, in addition to the vial aperture seal 270A, FIG. 2B also illustrates a facilitator seal assembly 272, e.g., a pair of O-rings that are configured to seal the connections between the cap access facilitator 266 and the collector body 253, e.g., at the top 253B of the collector body 253, and between the cap access facilitator 266 and the cap holder 264.

Still further, also shown in FIG. 2B is a parameter system inflow valve 274 that regulates flow of the fluid 24 from the fluid collector 230 to the fluid parameter testing system 232 (illustrated in FIG. 2A).

FIG. 2C is a simplified schematic front view illustration of the portion of the fluid sample collection system 212 illustrated in FIG. 2A. In particular, as noted above, in FIG. 2C, the sample vial assembly 256 and/or the sample vial 258 of the fluid collector 230 has been moved to the second position relative to the collector body 253 and/or passenger vial chamber 254.

As illustrated, when the sample vial 258 is in the second position, a majority of the sample vial 258 is positioned within the interior of the collector body 253 and/or the passenger vial chamber 254. More specifically, as shown in FIG. 2C, only a small portion of the sample vial 258 near the bottom the sample vial body 260 extends outside, and below, the passenger vial chamber 254 of the collector body 253. It is appreciated that, in certain embodiments, when in the second position, the sample vial 258 extends far enough below the collector body 253 so that the bottom of the sample vial body 260 can be easily grasped by a user for purposes of manipulating the positioning of the sample vial 258, e.g., rotating and/or moving translationally, relative to the collector body 253.

Further, as shown, when the sample vial 258 is in the second position, the cap access facilitator 266 engages the cap holder 264 of the sample vial 258. As provided herein, such engagement between the cap access facilitator 266 and the cap holder 264 enables the selective coupling and uncoupling between the sample vial body 260 and the vial cap 262. More specifically, in some embodiments, the cap access facilitator 266 is maintained in a fixed position within the upper portion of the passenger vial chamber 254 of the collector body 253 so as to effectively hold the cap holder 264 and thus the vial cap 262 in a fixed position. This enables the user to manipulate, e.g., screw or unscrew, the sample vial body 260 relative to the vial cap 262 to selectively couple or uncouple the vial cap 262 from the sample vial body 260. Additionally and/or alternatively, the operator can access the cap access facilitator 266 (and thus the cap holder 264 and the vial cap 262) via the antechamber 255 that surrounds the passenger vial chamber 254 to more effectively hold and maintain the position of the cap access facilitator 266 within the passenger vial chamber 254.

Figure 2D:
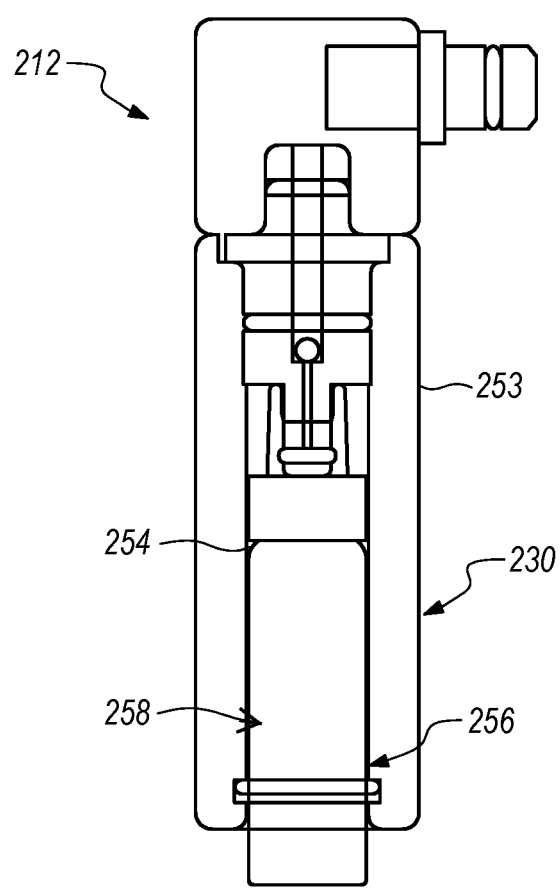
FIG. 2D is a simplified schematic side view illustration of the portion of the fluid sample collection system illustrated in FIG. 2A.

FIG. 2D is a simplified schematic side view illustration of the portion of the fluid sample collection system 212 illustrated in FIG. 2A. More specifically, similar to FIG. 2C, FIG. 2D again illustrates the fluid collector 230 with the sample vial assembly 256 and/or the sample vial 258 being in the second position relative to the passenger vial chamber 254 of the collector body 253.

Figure 2E:
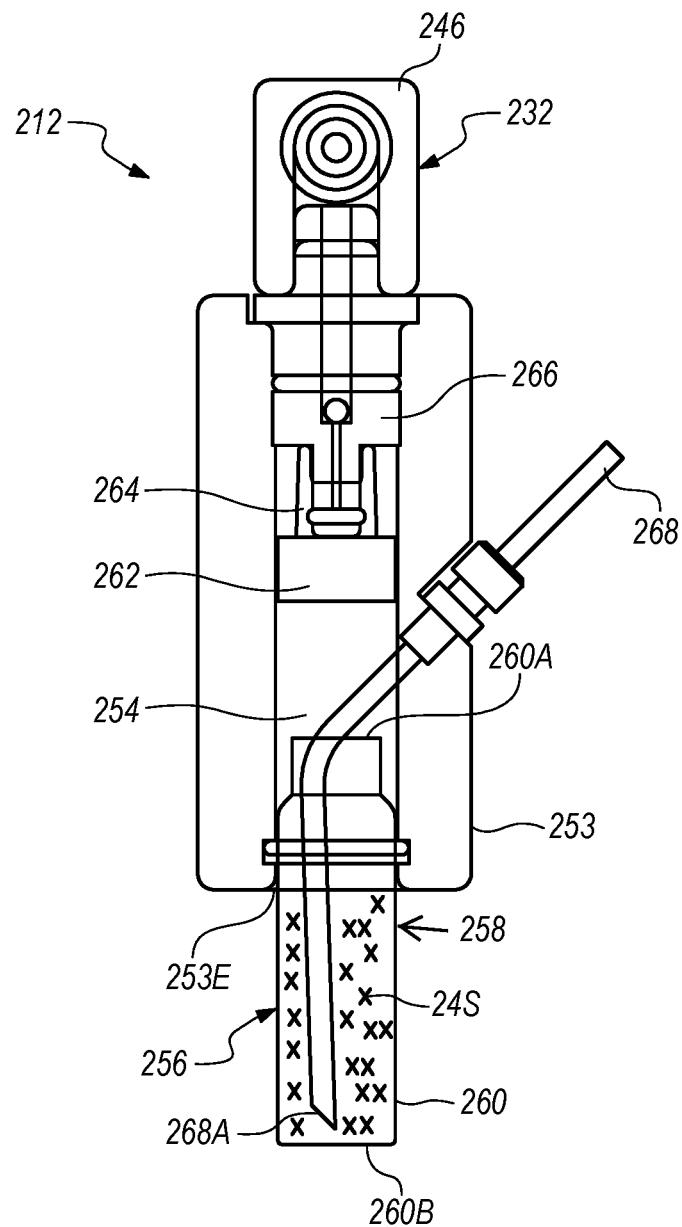
FIG. 2E is a simplified schematic front view illustration of the portion of the fluid sample collection system illustrated in FIG. 2A, the sample vial assembly being shown in a third position relative to the passenger vial chamber.

FIG. 2E is a simplified schematic front view illustration of the portion of the fluid sample collection system 212 illustrated in FIG. 2A. In particular, FIG. 2E illustrates the sample vial assembly 256 and/or the sample vial 258 being shown in a third position relative to the collector body 253 and/or the passenger vial chamber 254.

As shown in FIG. 2E, the vial cap 262 has been selectively removed or uncoupled from the sample vial body 260. Additionally, the vial cap 262 and the cap holder 264 are shown as being retained by the cap access facilitator 266 within the passenger vial chamber 254 of the collector body 253. For example, in one non-exclusive embodiment, the cap access facilitator 266 can engage the cap holder 264, and then the sample vial body 260 can be rotated relative to the collector body 253. As the cap holder 264 is being engaged, and held, by the cap access facilitator 266, rotation of the sample vial body 260 relative to the collector body 253 results in rotation of the sample vial body 260 relative to the vial cap 262. The sample vial body 260 can thus be uncoupled from the vial cap 262. It is appreciated that the uncoupling of the sample vial body 260 from the vial cap 262 can be accomplished in a different manner, i.e. other than simply unscrewing the sample vial body 260 from the vial cap 262.

Once the sample vial body 260 is uncoupled from the vial cap 262, the sample vial body 260, i.e. without the vial cap 262, can be moved in a generally downward direction away from the vial cap 262 and further out of the passenger vial chamber 254 of the collector body 253 so that the sample vial 258 is now open and ready to receive fluid 24 (illustrated in FIG. 1A) from the fluid source 10 (illustrated in FIG. 1A).

Also shown in FIG. 2E is the fluid pass-through vessel 268 through which the fluid 24 passes before entering the sample vial body 260. In some embodiments, the fluid pass-through vessel 268 can include a portion of one of the collector inlet lines 44 (illustrated in FIG. 1A) or a portion of the fluid return line 36 (illustrated in FIG. 1A). Alternatively, the fluid pass-through vessel 268 can be a fluid vessel, e.g., a tubular vessel, that is separate and distinct from both the collector inlet lines 44 and the fluid return line 36.

As noted above, in some embodiments, the fluid 24 from the fluid source 10 can be combined with a preservative from the preservation assembly 51 (illustrated in FIG. 1A) prior to the combined fluid 24 and preservative entering into the collector 230. Additionally, in such embodiments, the preservation assembly 51 and/or the preservative can be in fluid communication with the fluid pass-through vessel 268. In certain such embodiments, the preservative can be added to the fluid 24 directly within the fluid pass-through vessel 268. Alternatively, the preservative can be added to the fluid 24 prior to the fluid 24 reaching the fluid pass-through vessel 268.

In certain embodiments, the fluid pass-through vessel 268 can be configured and positioned to extend through a top opening 260A of the sample vial body 260 and have a vessel distal end 268A be positioned near a bottom 260B of the sample vial body 260. With such design, the fluid 24 will not splash significantly within and/or out of the sample vial body 260, and, as such, excessive air bubbles will not be formed within the fluid sample 24S to is collected within the sample vial body 260. Additionally, the bottom fill nature of this arrangement ensures that any contamination present on the interior of the collector body 253 is not entrained within the sample vial body 260.

During collection of the fluid sample 24S, the fluid 24 can be allowed to continue flowing after the sample vial body 260 has become completely filled. As the fluid 24 continues to flow, the fluid 24 will also eventually fill up the interior of the passenger vial chamber 254. The fluid 24 can then flow through the cap access facilitator 266, and into the fluid parameter testing system 232 via the parameter system inflow valve 274 (illustrated in FIG. 2B). The fluid parameter testing facilitator 246 can then combine excess fluid from multiple sample vials 258 (if more than one sample vial 258 is being used within the collection system 212) and move the excess fluid to the parameter testing cell 50 (illustrated in FIG. 1A) via the fluid testing line 48 (illustrated in FIG. 1A). The parameter testing cell 50 will then, as noted above, sense one or more parameters of the fluid 24 to ensure parameter stabilization. Once the fluid parameters have been stabilized, as confirmed by the parameter testing cell 50, the flow of fluid 24 from the fluid source 10 can be stopped, and the fluid pass-through vessel 268 can be removed from the sample vial 258. The sample vial body 260 can then be moved back to the second position, the sample vial body 260 can be moved, e.g., rotated, relative to the collector body 253, such that the vial cap 262 can again be coupled and sealed to the sample vial body 260.

At this time, the sample vial 258 can be removed from the passenger vial chamber 254 of the collector body 253 via the vial aperture 253E. The cap holder 264 can then be removed from the vial cap 262 so that the sample vial 258 conforms to the requirements of standard autosampler laboratory equipment. The sealed sample vial 258 can then be appropriately labeled and shipped to a laboratory for any desired testing of the fluid samples 24S.

Figure 3A:
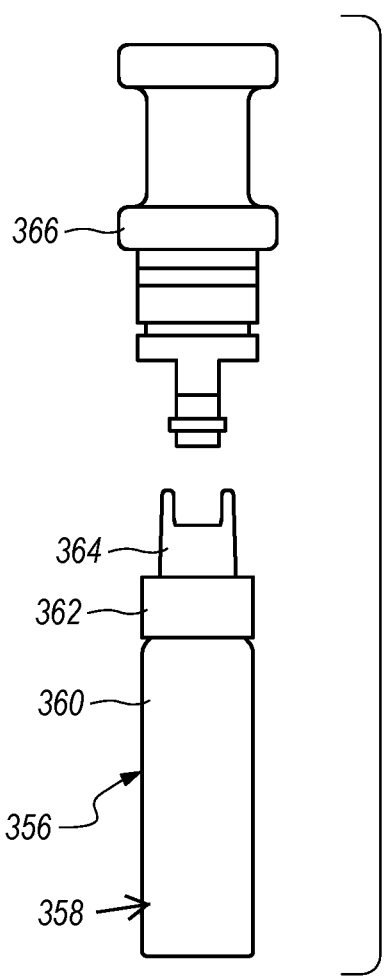
FIG. 3A is a simplified schematic view illustration of an embodiment of the sample vial assembly and an embodiment of a cap access facilitator that is shown prior to engagement with a sample vial of the sample vial assembly.

FIG. 3A is a simplified schematic view illustration of an embodiment of the sample vial assembly 356 and an embodiment of a cap access facilitator 366 that is shown prior to engagement with a sample vial 358 of the sample vial assembly 356.

As shown in FIG. 3A, the sample vial 358 includes the sample vial body 360, the vial cap 362 and the cap holder 364. The design and functioning of the sample body 360, the vial cap 362 and the cap holder 364 are substantially similar to what was illustrated and described herein above. Accordingly, a detailed description of such components will not be repeated herein.

Additionally, as noted, the cap access facilitator 366 is configured to selectively engage and retain the cap holder 364. The design of the cap access facilitator 366 can be varied to suit the requirements of the collection system 212 (illustrated in FIG. 2A).

Figure 3B:
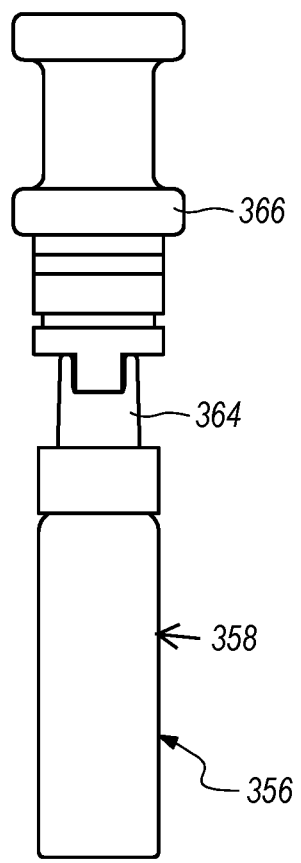
FIG. 3B is a simplified schematic view illustration of the sample vial assembly and the cap access facilitator illustrated in FIG. 3A, with the cap access facilitator shown engaging the sample vial of the sample vial assembly.

FIG. 3B is a simplified schematic illustration of the sample vial assembly 356 and the cap access facilitator 366 illustrated in FIG. 3A, with the cap access facilitator 366 shown engaging the sample vial 358 of the sample vial assembly 356. More particularly, in FIG. 3B, the sample vial 358 and the cap access facilitator 366 have been moved relative to one another so that the cap access facilitator 366 is now engaging and retaining (via a sealed engagement) the cap holder 364 of the sample vial 358.

Figure 4A:
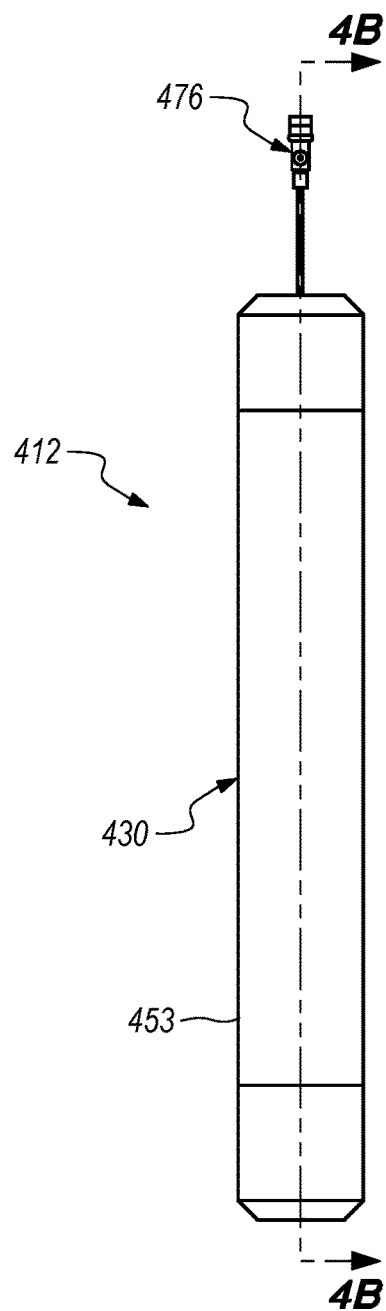
FIG. 4A is a simplified schematic view illustration of a portion of another embodiment of the fluid sample collection system.

FIG. 4A is a simplified schematic illustration of a portion of another embodiment of the fluid sample collection system 412. As illustrated in this embodiment, the collection system 412 can include a fluid collector 430 having a collector body 453, and a pressurization system 476 that is coupled in fluid communication to the collector body 453.

Figure 4B:
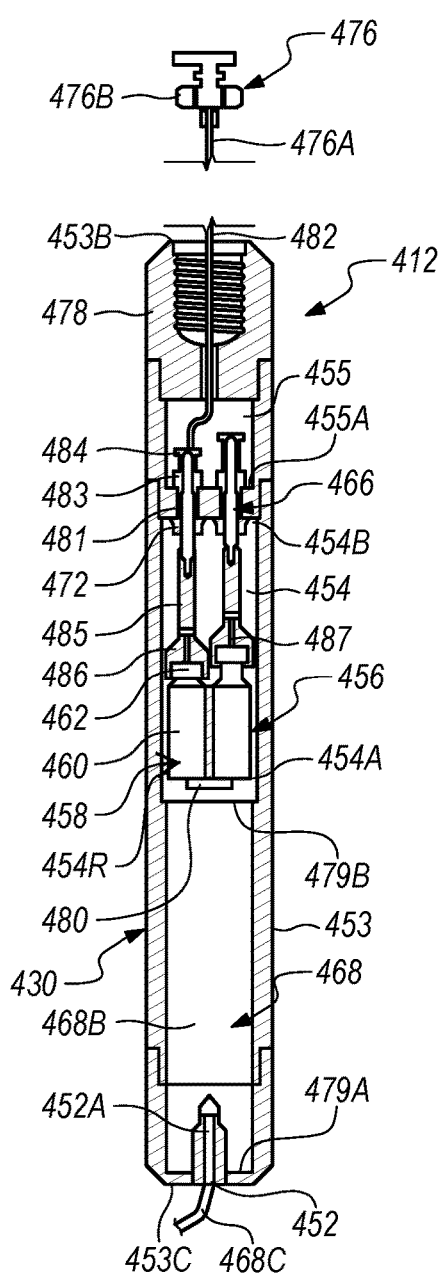
FIG. 4B is a sectional view of the portion of the fluid sample collection system taken on line 4B-4B in FIG. 4A.

FIG. 4B is a sectional view of the portion of the fluid sample collection system 412 taken on line 4B-4B in FIG. 4A. In particular, FIG. 4B illustrates many detailed features and aspects that can be included within the fluid collector 430 and the pressurization system 476. As illustrated in FIG. 4B, the fluid collector 430 is somewhat similar to what was illustrated and described above in the previous embodiments, although the specific design, functioning and positioning of the various components of the fluid collector 430 are somewhat different than in the previous embodiments. For example, in the embodiment shown in FIG. 4B, the fluid collector 430 includes a system fluid inflow conduit 452 (an "inflow conduit"), a collector body 453 that defines and/or includes a passenger vial chamber 454 and an antechamber 455, a sample vial assembly 456 including at least one sample vial 458 (two are shown in FIG. 4B) having a sample vial body 460 and a sample vial cap 462, and a cap access facilitator 466. Additionally, the fluid collector 430 again includes a fluid pass-through vessel 468 through which the fluid 24 (illustrated in FIG. 1A) flows prior to the fluid 24 entering the sample vial 458, i.e. the sample vial body 460. However, in this embodiment, the fluid pass-through vessel 468 is provided in the form of a host container 468B that is further defined by and/or included within the collector body 430, in addition to the tubular vessel 468C, e.g., a portion of one of the collector inlet lines 44 (illustrated in FIG. 1A), a portion of the fluid return line 36 (illustrated in FIG. 1A), or a separate tubular vessel, that is configured to extend into an interior of the collector body 430.

As shown, the passenger vial chamber 454 is configured to selectively receive and retain the at least one sample vial 458. For example, the passenger vial chamber 454 can include at least on vial receptacle 454R, with each vial receptacle 454R being configured to receive a sample vial 458. In the case of two or more sample vials 458, the sample vials 458 can reside inside the passenger vial chamber 454 in a side-by-side configuration or in an over-under configuration, i.e. stacked on top of one another. Other internal configurations for the sample vials 458 of the collection system 412 include vertically right-side up, vertically upside down, angled and horizontal within the passenger vial chamber 454. It is appreciated that the passenger vial chamber 454 can be configured to selectively receive and retain any suitable number of sample vials 458.

In this embodiment, the host container 468B, the passenger vial chamber 454, the antechamber 455, and a deployment head 478 are selectively coupled to one another to make up the collector body 453. As shown in FIG. 4B, the collector body 453 is configured with the passenger vial chamber 454 positioned between the host container 468B and the antechamber 455 while the collection system 412 is receiving fluid 24 that has been pumped with the pump 34 (illustrated in FIG. 1A) from the fluid source 10 (illustrated in FIG. 1A). Stated in another manner, in the embodiment shown in FIG. 4B, the uppermost compartment of the collection system 412 is referred to as the antechamber 455; the next lower compartment is referred to as the passenger vial chamber 454; and the lowest of the three compartments is referred to as the host container 468B. As provided herein, the antechamber 455 allows one to remotely access the passenger vial chamber 454 to operate the cap access facilitator 466 within the passenger vial chamber 454 below the antechamber 455. Additionally, in this embodiment, the deployment head 478 is selectively coupled to the antechamber 455. Further, as provided herein, at certain times during the use of the collection system 412, the various components of the collector body 453 can be uncoupled from one another, e.g., during removal of the sample vials 458 from within the collector body 453. Alternatively, the collector body 453 and/or the components thereof can be configured in another manner than that illustrated in FIG. 4B.

In this embodiment, the tubular vessel 468C of the fluid pass-through vessel 468, e.g., the fluid return line 36 (illustrated in FIG. 1A) that extends from the pump 34 to the fluid collector 430, one of the collector inlet lines 44, or a separate tubular vessel, is connected to the inflow conduit 452 at or near a base 479A of the host container 468B. Additionally, as shown, the base 479A of the host container 468B substantially coincides with the base 453C of the collector body 453. With such design, the fluid 24 can fill the host container 468B from the bottom up. Thus, as noted above, in this embodiment, the tubular vessel 468C and the host container 468B work in conjunction with one another to function as the fluid pass-through vessel 468 through which the fluid 24 passes before entering the sample vial 458 and/or the passenger vial chamber 454.

In some embodiments, the fluid 24 flows into the host container 468B through the inflow conduit 452, which can be regulated through the use of an inflow valve 452A, e.g., a one-way valve, that is positioned adjacent to the inflow conduit 452 at or near the base 479A of the host container 468B.

As the fluid 24 continues to fill up the host container 468B, the fluid 24 eventually reaches a top 479B of the host container 468B. The fluid 24 then continues to fill upwardly into the passenger vial chamber 454 through a chamber inflow regulator 480, e.g., a one-way valve or other suitable type of valve, or a chamber aperture, at a chamber bottom 454A. Thus, the fluid 24 flows into the passenger vial chamber 454 via the chamber inflow regulator 480 that is positioned at the chamber bottom 454A.

Additionally, as the fluid 24 continues to flow upwardly into the passenger vial chamber 454 so as to fill the passenger vial chamber 454, the fluid 24 further flows into the sample vial(s) 458. More particularly, during the actual collection of the fluid samples 24S (illustrated in FIG. 2E), the vial cap 462 is not coupled to the sample vial body 460 such that the sample vial body 460 is effectively open for purposes of receiving the fluid samples 24S therein. Further, as the fluid 24 continues to flow into the passenger vial chamber 454 to fill the passenger vial chamber 454, the atmosphere inside the passenger vial chamber 454 is displaced by the infilling fluid 24. In such case, the displaced atmosphere can escape through a chamber top 454B of the passenger vial chamber 454, and can then travel through an upper chamber valve 481 at the chamber top 454B and/or a vent 482 at a top 453B of the collector body 453.

The host container 468B and the passenger vial chamber 454 can be made of any material including any type of plastic, steel, fiberglass, composites or any other suitable material and can have any diameter, height and geometric form.

With respect to fill detection of the host container 468B and the passenger vial chamber 454, and the sample vials 458 contained therein, there are several methods and/or apparatuses for doing so. For example, as the host container 468B and passenger vial chamber 454 are filling with fluid 24 from the fluid source 10, the atmosphere inside the host container 468B and passenger vial chamber 454 are displaced by the infilling fluid 24, moving from the bottom to the top of the collection system 412. The displaced gas exits through the upper chamber valve 481 at the chamber top 454B and/or the vent 482 located at the top 453B of the collector body 453. If there is no more atmosphere left inside the host container 468B and the passenger vial chamber 454, then only fluid 24 will exit through the upper chamber valve 481 and/or the vent 482. Upon first arrival of fluid 24 exiting through the upper chamber valve 481 and/or the vent 482, the pump 34 can be stopped, and/or the inflow valve 452, the chamber inflow regulator 480 and/or the upper chamber valve 481 can be closed such that the host container 468B and the passenger vial chamber 454 are sealed off from external atmospheric contact. If desired at this point, the collection system 412 can be re-pressurized in order to simulate the hydrostatic pressure at the sample depth of the pump 34.

The antechamber 455 allows remote closure of the sample vials 458 within the passenger vial chamber 454, i.e. through use of the cap access facilitator 466 as described below, without substantially exposing the sample vials 458 to the external atmosphere surrounding the collection system 412. This configuration also inhibits fluid 24 from entering the antechamber 455 at any point in time—either before, during or after the sample vials 458 are filled with the fluid 24 to comprise the desired fluid samples 24S. In certain embodiments, this can be accomplished through internally bypassing the antechamber 455 with a pressurization line 476A that enters through the top 453B of the collector body 453, coaxially passes through the antechamber 455 entirely and then connects to a tube fitting 483 on an antechamber floor 455A of the antechamber 455. Therefore, the internal environment inside the pressurization line 476A does not come into contact with the environment of the antechamber 455. At the connection point, the pathway then continues through the antechamber floor 455A of the antechamber 455 (simultaneously the chamber top 454B of the passenger vial chamber 454) and terminates where the pressurization line 476A exits into the passenger vial chamber 454 itself.

In certain embodiments, the collection system 412 can utilize the pressurization system 476 to provide a desired environment within the collector body 453, i.e. to permit pressurization as well as depressurization when required. For example, in some such embodiments, the host container 468B and/or the passenger vial chamber 454 can be pressurized with an inert gas, compressed air, or another suitable fluid prior to receiving the fluid 24 from the fluid source 10. The desired inert gas, compressed air, or other suitable fluid can be provided into the passenger vial chamber 454 and/or the host container 458B via the pressurization line 476A, as regulated by a pressurization valve 476B. The inert gas environment created inside the host container 468B and/or the passenger vial chamber 454 has several advantages including reduction or elimination of an oxidizing environment in contact with the fluid sample 24S that is being collected with the collection system 412. Additionally, the inert gas from the pressurization system 476 can also be used to control the rate at which the sample vials 458 are being filled with the fluid samples 24S. When the fluid sample 24S is ready to be delivered by the pump 34 located at some depth inside the fluid source 10, the host container 468B and/or the passenger vial chamber 454 can be depressurized either completely or partially in order to allow the fluid sample 24S to fill the sample vials 458 to a desired fill level. Once the sample vials 458 have reached the desired fill level, compressed gas can then be reintroduced and used to reconstitute simulation of the hydrostatic pore pressure from which the fluid sample 24S was obtained. Alternatively, the collection system 412 can be utilized without the pressurization system 476.

As shown, the internal pressure of the host container 468B and the passenger vial chamber 454 are locked-in between the inflow valve 452A and the chamber inflow regulator 480, and/or between the chamber inflow regulator 480 and the upper chamber valve 481.

Additionally, in certain embodiments, a portion of the collection system 412, e.g., the fluid collector 430, can supported by a device stand (not shown), e.g., a rack, a tripod, or the like) to inhibit the fluid collector 430 from tipping over as well as to raise the fluid collector 430 above a working surface so as not to allow surficial contact with the working surface to avoid being influenced by the surface temperature.

As provided herein, the cap access facilitator 466 can be configured to selectively access the vial cap 462 of the sample vial 458 to selectively open and close the sample vial 458, i.e. so that the vial cap 462 is selectively coupled to and uncoupled from the sample vial body 460. The design of the cap access facilitator 466 and the vial cap 462 can be varied. For example, in some embodiments, the cap access facilitator 466 and the vial cap 462 can formulate a slot and key system that assures that the sample vial body 460 and the vial cap 462 are correctly oriented within the vial receptacle 454R. Correct orientation of the sample vial body 460 and the vial cap 462 within the vial receptacle 454R inhibits potential cross-threading of the vial cap 462 when the vial cap 462 is remotely screwed onto the sample vial body 460, and further inhibits air bubbles from entering a given fluid sample 24S during packaging in the field and transport to a suitable laboratory.

Prior to collecting the fluid samples 24S, the deployment head 478 is removed from the remainder of the collector body 453 to provide access to the interior of the antechamber 455. In one embodiment, the antechamber floor 455A of the antechamber 455 includes twist knobs 484 as part of the cap access facilitator 466 that can be operated with an Allen-wrench, screw driver, or another suitable tool. The twist knobs 484 are connected to a rotational armature 485 that extends through the antechamber floor 455A of the antechamber 455, passing through facilitator seal assembly 472, e.g., a plurality of O-rings), and exits into the passenger vial chamber 454. The bottom end fixtures for each rotational armature 485 include a vial cap clamp 486. In certain embodiments, the vial cap 462 resides within the vial cap clamp 486. The vial cap 462 is held in place with either a set screw 487 that is controlled from the side of the vial cap clamp 486, or through an interlocking geometry. In various embodiments, one element to the vial cap clamp 486, vial cap 462, sample vial body 460 and vial receptacle 454R is the use of the key and slot alignment system that orients each sample vial 458 into only a single loading position. For example, in one non-exclusive embodiment, the vial cap 462 contains two vertical slots that can be separated by approximately one hundred eighty degrees and can be oriented vertically along a height of the vial cap 462. In one embodiment, the vial cap clamp 486 receives the vial cap 462 and contains internal vertical keys that fit into the slots and are also oriented at approximately one hundred eighty degrees apart. The sample vial 458 can have two vertical slots as well that run a vertical height of the sample vial 458. The sample vial 458 can slide into the vial receptacle 454R that contains the two corresponding keys that align with the vial slots.

When it is desired to open the sample vial 458 for purposes of receiving the desired fluid samples 24S, the twist knobs 484 in the antechamber 455 are rotated, and the armature 485 as well as the vial cap clamp 486 rotates accordingly whereby the vial cap 462 is threaded off of the corresponding sample vial body 460. In the embodiment illustrated and described herein, the twist knobs 484, the rotational armatures 485, the vial cap clamps 486, and the set screws 487 can be said to be included as components of the cap access facilitator 466.

Upon filling of the sample vials 458, the deployment head 478 can again be removed from the remainder of the collector body 453 to again provide access to the antechamber 455. Once the deployment head 478 is removed, the twist knobs 484 can again be accessed and operated. When the twist knobs 484 in the antechamber 455 are rotated, the armature 485 as well as the vial cap clamp 486 rotates accordingly whereby the vial cap 462 is threaded onto the corresponding sample vial body 460. In so doing, atmospheric contact with the fluid samples is inhibited or prevented, direct human contact with the fluid 24 in the passenger vial chamber 454 and/or the sample vials 458 is inhibited or prevented, and transfer of fluid 24 from the sample vials 458 to another container prior to shipment to an analytical lab can be avoided. The key and slots for both the vial cap 462 and sample vial 458 section of the collection system 412 inhibit any rotational slippage during vial cap 462 rotation where it is being threaded on to the top of the sample vial body 460.

The entire vial cap 462 and sample vial 458 design can also provide another benefit. When both the vial cap 462 and the sample vial body 460 of the sample vial 458 are completely submerged under fluid inside the passenger vial chamber 454 of the collection system 412, there is a possibility that a few remaining air bubbles could reside inside the vial cap 462. The process of threading the vial cap 462 onto the sample vial body 460 can force any remaining air bubbles to be removed from the vial cap 462 by displacement of the air bubbles by the sample vial body 460 and the threads of the vial cap 462, and the volume of fluid 24 inside the passenger vial chamber 454 when the threads are fully mated together via the threading procedure.

As provided herein, in this embodiment, once the fluid 24 has been received into the collection system 412 and fills the sample vial(s) to provide the desired fluid sample(s) 24S, the passenger vial chamber 454 and/or the antechamber 455 can be removed/detached from the host container 468B without transfer of the fluid samples 24S in the passenger vial chamber 454 to another container. The passenger vial chamber 454 can then be labeled (such as by a field technician) and placed inside of a shipment container for transportation to an analytical laboratory. Additionally, or in the alternative, in some embodiments, the sample vials 458 can be removed from the passenger vial chamber 454 and independently sealed, and the individual sample vials 458 can then be shipped to a laboratory for desired analysis.

Additionally, in one embodiment, each vial cap 462 contains a septum (not shown in FIG. 5B). One purpose of the septum is so that when the passenger vial chamber 454 reaches the lab, the sample vials 458 are then inserted into a receiving tray, typically one that can host many such sample vials 458. A small sample of the fluid sample 24S is extracted from each of the sample vials 458, often times via a robotic arm that travels to each sample vial 458, whereby, following the arrival, the robotic arm inserts a needle through the septum in order to extract a small subsample of the fluid sample 24S inside the sample vial 458. The sample is then analyzed by various methods. If the sample vials 458 are made from stainless steel, they typically can be reused by first applying proper cleaning methods before the reuse.

FIG. 5A is a simplified schematic illustration of another embodiment of the sample vial assembly 456 and another embodiment of a portion of the cap access facilitator 466 that is shown prior to engagement with a sample vial 458 of the sample vial assembly 456.

As shown in FIG. 5A, the sample vial 458 includes the sample vial body 460 and the vial cap 462. Additionally, as noted above, the cap access facilitator 466 is configured to selectively engage and retain the vial cap 462.

FIG. 5B is a simplified schematic illustration of the sample vial assembly 456, e.g., the sample vial 458, and the portion of the cap access facilitator 466 illustrated in FIG. 5A, with the cap access facilitator 466 shown in the process of coupling the vial cap 462 to the sample vial body 460.

Figure 6:
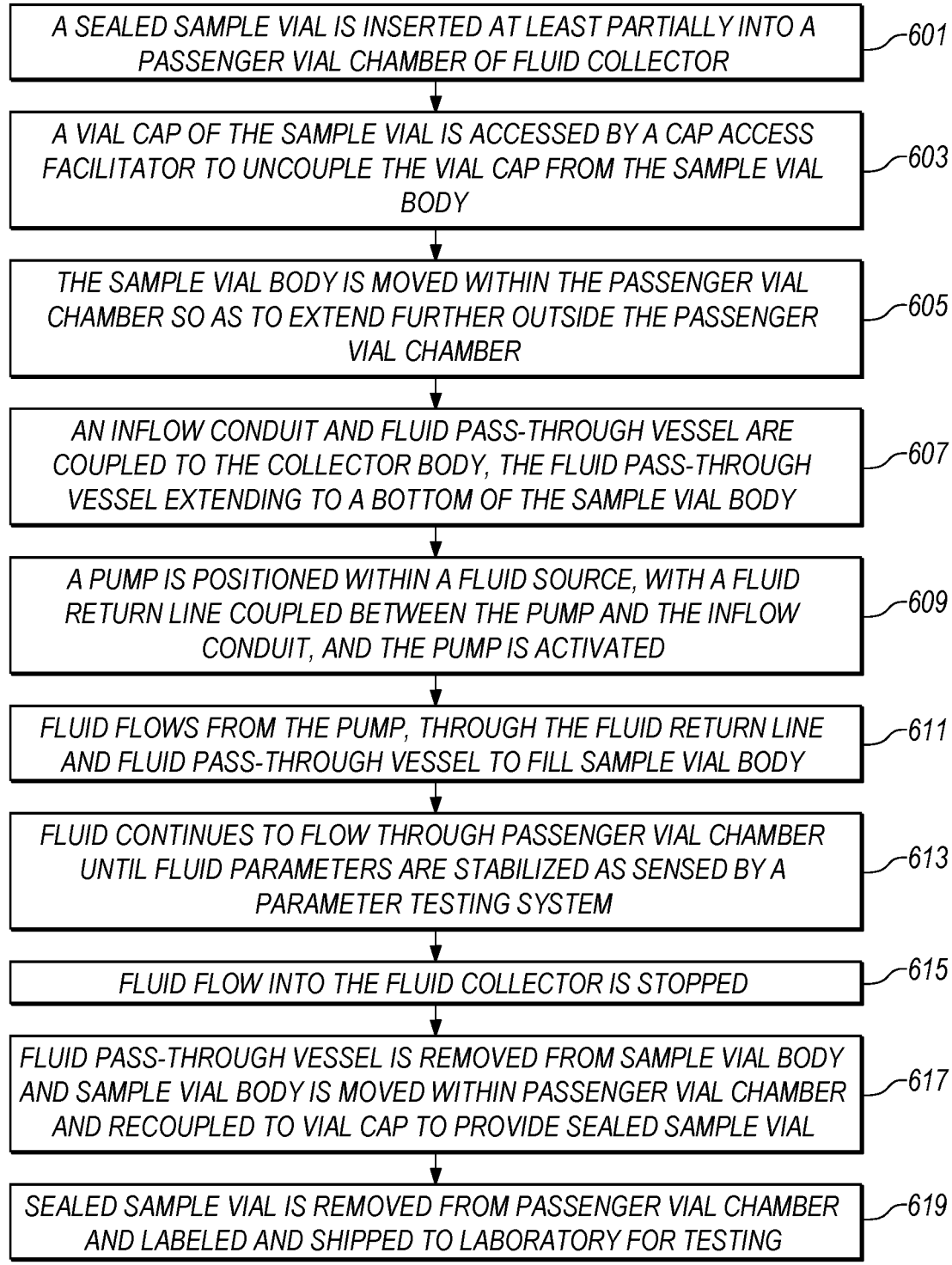
FIG. 6 is a simplified flowchart illustrating one representative example of the procedure for removing a fluid sample from a fluid source utilizing the fluid sample collection system.

FIG. 6 is a simplified flowchart illustrating one representative example of the procedure for removing a fluid sample from a fluid source utilizing the fluid sample collection system. It is appreciated that the various steps illustrated and described herein can be performed in any suitable order, and any steps can be combined, omitted, and/or performed substantially simultaneously with any other steps without deviating from the intended breadth and scope of the present invention.

At step 601, a sample vial with the vial cap secured to the sample vial body is inserted at least partially into a passenger vial chamber of a collector body of a fluid collector. In some embodiments, the sample vial is positioned in the passenger vial chamber via a vial access aperture that is formed in the collector body.

At step 603, the vial cap is engaged by a cap access facilitator, and the vial cap is uncoupled from the sample vial body.

At step 605, the sample vial body is moved within the passenger vial chamber, so that the sample vial body extends further outside of the passenger vial chamber and/or the collector body.

At step 607, a system fluid inflow conduit is coupled to the collector body so as to extend through a fluid aperture formed in the collector body. Additionally, a fluid pass-through vessel is positioned to extend through a conduit aperture formed in the system fluid inflow conduit so that a vessel distal end of the fluid pass-through vessel is positioned near a bottom of the sample vial body.

At step 609, a pump is positioned in a fluid source from which fluid samples are desired. A fluid return line is coupled to the pump and extends between the pump and the system fluid inflow conduit. Once the pump and the fluid return line are positioned as desired, the pump is activated so as to pump the fluid from the fluid source.

At step 611, the fluid flows from the pump, through the fluid return line, through the fluid pass-through vessel and into the sample vial body, so as to fill the sample vial body with fluid from the fluid source.

At step 613, the fluid is allowed to continue flowing to fill the passenger vial chamber. As the fluid continues to flow after the passenger vial chamber has been filled, the excess fluid is directed out of the passenger vial chamber toward a parameter testing system. One or more fluid parameters are sensed and/or tested in the excess fluid until such time as the fluid parameters become stabilized. At such time, the operator would be satisfied that the fluid sample in the sample vial retains no remnant characteristic of the sample vial or its initial atmosphere.

At step 615, the pump is turned off or the fluid is otherwise stopped from flowing from the fluid source into the fluid collector.

At step 617, the fluid pass-through vessel is removed from the sample vial body and/or is taken out of the collector body. The sample vial body is then moved within the passenger vial chamber back toward the vial cap. The vial cap is again accessed by the cap access facilitator so that the vial cap is effectively coupled and sealed to the sample vial body.

At step 619, the sealed sample vial is removed from the passenger vial chamber and/or the collector body, e.g., via the vial access aperture. The sealed sample vial is then appropriately labeled and shipped to a suitable laboratory for any desired testing of the fluid samples retained therein.

It is understood that although a number of different embodiments of the fluid sample collection system 12 have been illustrated and described herein, one or more features of any one embodiment can be combined with one or more features of one or more of the other embodiments, provided that such combination satisfies the intent of the present invention.

While a number of exemplary aspects and embodiments of the fluid sample collection system 12 have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A fluid sample collection system for directly collecting a fluid sample from a fluid source without exposing the fluid sample to an ambient environment that surrounds the fluid sample collection system, the fluid sample collection system comprising:
- a fluid collector including:
  - (i) a sample vial that is configured to retain fluid from the fluid source, the sample vial including a sample vial body and a vial cap that is selectively coupled and sealed to the sample vial body;
  - (ii) a collector body that defines a passenger vial chamber, the sample vial being positioned at least partially within the passenger vial chamber during collection of the fluid; and
  - (iii) a cap access facilitator that is configured to engage a portion of the sample vial to enable a user to selectively couple the vial cap to the sample vial body to seal the sample vial so that the fluid is retained within the sample vial; and
- a second fluid collector that is coupled to the fluid collector, the second fluid collector including (i) a second sample vial that is configured to retain fluid from the fluid source, the second sample vial including a second sample vial body and a second vial cap that is selectively coupled and sealed to the second sample vial body; (ii) a second collector body that defines a second passenger vial chamber that is configured to selectively retain the second sample vial during collection of the fluid; and (iii) a second cap access facilitator that is configured to engage a portion of the second sample vial to enable a user to selectively couple the second vial cap to the second sample vial body to seal the second sample vial so that the fluid is retained within the second sample vial.

2. The fluid sample collection system of claim 1 further comprising a fluid pass-through vessel that is configured to extend through an aperture in the collector body, the fluid pass-through vessel providing a conduit through which the fluid flows from outside the collector body and into the sample vial body.

3. The fluid sample collection system of claim 2 wherein the fluid enters the fluid pass-through vessel after the fluid has been removed from the fluid source, but prior to the fluid entering the sample vial body.

4. The fluid sample collection system of claim 2 wherein the fluid collector further includes a system fluid inflow conduit that is configured to be positioned within and extend through the aperture in the collector body, the fluid pass-through vessel being configured to extend through the system fluid inflow conduit, the fluid pass-through vessel including a vessel distal end that is configured to be positioned near a bottom of the sample vial body.

5. The fluid sample collection system of claim 2 further comprising a preservation assembly that is coupled in fluid communication to the fluid pass-through vessel, the preservation assembly being configured to selectively add a preservative to the fluid from the fluid source.

6. The fluid sample collection system of claim 1 further comprising a distribution system that receives fluid from the fluid source, the distribution system being configured to distribute fluid to each of the fluid collector and the second fluid collector.

7. The fluid sample collection system of claim 1 further comprising a fluid parameter testing system that is configured to receive excess fluid from the fluid collector, the fluid parameter testing system including a sensor that is configured to sense at least one fluid parameter of the excess fluid that is received from the fluid collector.

8. The fluid sample collection system of claim 1 further comprising a pump assembly that pumps the fluid out of the fluid source and directs the fluid to the fluid collector.

9. The fluid sample collection system of claim 1 wherein the passenger vial chamber is configured to selectively retain a plurality of sample vials simultaneously.

10. The fluid sample collection system of claim 1 wherein the passenger vial chamber is formed from a non-rigid material.

11. The fluid sample collection system of claim 1 wherein the collector body further defines an antechamber that is positioned substantially adjacent to the passenger vial chamber, the antechamber being configured to provide access to the cap access facilitator for the user, the antechamber not being in fluid communication with the passenger vial chamber.

12. The fluid sample collection system of claim 1 wherein the sample vial further includes a cap holder that is coupled to the vial cap; and wherein the cap access facilitator is configured to selectively engage and retain the cap holder during selective coupling between the vial cap and the sample vial body.

13. The fluid sample collection system of claim 1 wherein the collector body includes a vial aperture; wherein the sample vial is moved into and out of the passenger vial chamber through the vial aperture; and wherein the fluid collector further includes a vial aperture seal that seals a connection between the sample vial and the collector body when the sample vial is positioned at least partially within the passenger vial chamber.

14. A fluid sample collection system for directly collecting a fluid sample from a fluid source without exposing the fluid sample to an ambient environment that surrounds the fluid sample collection system, the fluid sample collection system comprising:
- a fluid collector including (i) a sample vial that is configured to retain fluid from the fluid source, the sample vial including a sample vial body and a vial cap that is selectively coupled and sealed to the sample vial body; (ii) a collector body that defines a passenger vial chamber, the sample vial being positioned at least partially within the passenger vial chamber during collection of the fluid; and (iii) a cap access facilitator that is configured to engage a portion of the sample vial to enable a user to selectively couple the vial cap to the sample vial body to seal the sample vial so that the fluid is retained within the sample vial;
- a pump assembly that pumps the fluid out of the fluid source and directs the fluid to the fluid collector;
- a system fluid inflow conduit that is configured to be positioned within and extend through an aperture in the collector body;
- a fluid pass-through vessel that is configured to extend through the system fluid inflow conduit, the fluid pass-through vessel providing a conduit through which the fluid flows from outside the collector body and into the sample vial body, the fluid entering the fluid pass-through vessel after the fluid has been removed from the fluid source, but prior to the fluid entering the sample vial body; and
- a fluid parameter testing system that is configured to receive excess fluid from the fluid collector, the fluid parameter testing system including a sensor that is configured to sense at least one fluid parameter of the excess fluid that is received from the fluid collector.

15. The fluid sample collection system of claim 14 further comprising a preservation assembly that is coupled in fluid communication to the fluid pass-through vessel, the preservation assembly being configured to selectively add a preservative to the fluid from the fluid source.

16. The fluid sample collection system of claim 14 wherein the passenger vial chamber is configured to selectively retain a plurality of sample vials simultaneously.

17. The fluid sample collection system of claim 14 wherein the collector body further defines an antechamber that is positioned substantially adjacent to the passenger vial chamber, the antechamber being configured to provide access to the cap access facilitator for the user, the antechamber not being in fluid communication with the passenger vial chamber.

18. The fluid sample collection system of claim 14 wherein the sample vial further includes a cap holder that is coupled to the vial cap; and wherein the cap access facilitator is configured to selectively engage and retain the cap holder during selective coupling between the vial cap and the sample vial body.

19. The fluid sample collection system of claim 14 wherein the collector body includes a vial aperture; wherein the sample vial is moved into and out of the passenger vial chamber through the vial aperture; and wherein the fluid collector further includes a vial aperture seal that seals a connection between the sample vial and the collector body when the sample vial is positioned at least partially within the passenger vial chamber.

20. A fluid sample collection system for directly collecting a preserved fluid sample from a raw fluid source without exposing the preserved fluid sample to an ambient environment that surrounds the fluid sample collection system, the fluid sample collection system comprising:
　a fluid collector including (i) a sample vial that is configured to retain preserved fluid from the raw fluid source, the sample vial including a sample vial body and a vial cap that is selectively coupled and sealed to the sample vial body; (ii) a collector body that defines a passenger vial chamber, the sample vial being positioned at least partially within the passenger vial chamber during collection of the fluid; and (iii) a cap access facilitator that is configured to engage a portion of the sample vial to enable a user to selectively couple the vial cap to the sample vial body to seal the sample vial so that the fluid is retained within the sample vial;
　a fluid mover that moves the raw fluid from the raw fluid source toward the fluid collector;
　a system fluid inflow conduit that is configured to be positioned within and extend through an aperture in the collector body;
　a fluid pass-through vessel that is configured to extend through the system fluid inflow conduit, the fluid pass-through vessel providing a conduit through which the fluid flows from outside the collector body and into the sample vial body, the fluid entering the fluid pass-through vessel after the fluid has been removed from the fluid source, but prior to the fluid entering the sample vial body; and
　a preservative assembly that is in fluid communication with the fluid pass-through vessel, the preservative assembly being configured to selectively add preservative material to raw fluid from the raw fluid source to provide the preserved fluid.

21. The fluid sample collection system of claim 20 further comprising a fluid parameter testing system that is configured to receive excess fluid from the fluid collector, the fluid parameter testing system including a sensor that is configured to sense at least one fluid parameter of the excess fluid that is received from the fluid collector.

22. The fluid sample collection system of claim 20 wherein the passenger vial chamber is configured to selectively retain a plurality of sample vials simultaneously.

23. The fluid sample collection system of claim 20 wherein the collector body further defines an antechamber that is positioned substantially adjacent to the passenger vial chamber, the antechamber being configured to provide access to the cap access facilitator for the user, the antechamber not being in fluid communication with the passenger vial chamber.

24. The fluid sample collection system of claim 20 wherein the sample vial further includes a cap holder that is coupled to the vial cap; and wherein the cap access facilitator is configured to selectively engage and retain the cap holder during selective coupling between the vial cap and the sample vial body.

25. The fluid sample collection system of claim 20 wherein the collector body includes a vial aperture; wherein the sample vial is moved into and out of the passenger vial chamber through the vial aperture; and wherein the fluid collector further includes a vial aperture seal that seals a connection between the sample vial and the collector body when the sample vial is positioned at least partially within the passenger vial chamber.

* * * * *